United States Patent
Urakabe

(10) Patent No.: US 12,016,989 B2
(45) Date of Patent: Jun. 25, 2024

(54) PERCUTANEOUS TERMINAL FOR HEMODIALYSIS AND INDIVIDUALIZED HEMODIALYSIS SYSTEM

(71) Applicant: KABUSHIKI KAISYA ADVANCE, Tokyo (JP)

(72) Inventor: Nobuchika Urakabe, Tokyo (JP)

(73) Assignee: KABUSHIKI KAISYA ADVANCE, Tokyo (JP)

( * ) Notice: Subject to any disclaimer, the term of this patent is extended or adjusted under 35 U.S.C. 154(b) by 683 days.

(21) Appl. No.: 17/255,083

(22) PCT Filed: Jul. 1, 2019

(86) PCT No.: PCT/JP2019/026194
§ 371 (c)(1),
(2) Date: Dec. 22, 2020

(87) PCT Pub. No.: WO2020/004672
PCT Pub. Date: Jan. 2, 2020

(65) Prior Publication Data
US 2021/0299344 A1    Sep. 30, 2021

(30) Foreign Application Priority Data
Jun. 29, 2018   (JP) .................... 2018-124023

(51) Int. Cl.
*A61M 1/36* (2006.01)
*A61M 1/38* (2006.01)

(52) U.S. Cl.
CPC ........ *A61M 1/3661* (2014.02); *A61M 1/3639* (2013.01); *A61M 1/38* (2013.01); *A61M 2205/3334* (2013.01)

(58) Field of Classification Search
CPC .... A61M 1/3661; A61M 1/3639; A61M 1/38; A61M 2205/3334; A61M 39/04;
(Continued)

(56) References Cited

U.S. PATENT DOCUMENTS

| 4,898,669 A | 2/1990 | Tesio |
| 5,026,397 A | 6/1991 | Aoki et al. |

(Continued)

FOREIGN PATENT DOCUMENTS

| JP | S60-92768 A | 5/1985 |
| JP | S61-179163 A | 8/1986 |

(Continued)

OTHER PUBLICATIONS

Tanaka, et al., "Study of Variations in Circulation Blood Volume and Automated Control of Ultrafiltration Rate Using a New Monitoring System During Hemodialysis", Japanese Journal of Artificial Organs, 28(2), 339-344, 1999 (English Abstact).

(Continued)

*Primary Examiner* — Ariana Zimbouski
*Assistant Examiner* — Rachel T. Smith
(74) *Attorney, Agent, or Firm* — LEWIS ROCA ROTHGERBER CHRISTIE LLP

(57) ABSTRACT

According to the present invention, blood access formed by a percutaneous terminal for hemodialysis is performed, the percutaneous terminal provided with: a contact body comprising a biocompatible member that comes into contact with skin tissue inside and outside a living body; a tubular body having one end connected to an artery and the other end connected to a vein; a blood removal tubular body having one end connected to a side surface of the tubular body and supplying blood to an external blood circuit; and a retransfusing tubular body having one end connected to the vein and the other end connected to a retransfusing portion of the blood circuit, wherein the other end of the blood removal tubular body and the retransfusing tubular body are located at a central portion of the contact body. Furthermore, provided is a hemodialysis system that is less burdensome for a patient and enables stable blood access.

6 Claims, 29 Drawing Sheets

(58) Field of Classification Search
CPC .. A61M 2039/0258; A61M 2039/0264; A61M 2039/0276; A61M 2039/0282; A61M 2039/0288; A61M 1/3403; A61M 2205/3306; A61M 2205/3576; A61M 1/1601; A61M 2205/52; A61M 2230/30; A61M 1/3653; A61M 1/3659; A61M 39/0247; A61M 1/3655; A61M 5/14276; A61M 1/3601; A61M 1/3621; A61M 1/3622–3623

See application file for complete search history.

(56) References Cited

U.S. PATENT DOCUMENTS

| | | | |
|---|---|---|---|
| 9,174,037 | B2 | 11/2015 | Schutz et al. |
| 2001/0049488 | A1 | 12/2001 | Kawamura |
| 2004/0122346 | A1* | 6/2004 | Kawamura ......... A61M 1/3661 604/4.01 |
| 2007/0293848 | A1 | 12/2007 | Endo et al. |
| 2009/0306599 | A1 | 12/2009 | Furuzono et al. |
| 2010/0152640 | A1* | 6/2010 | Golding ............. A61M 1/3656 604/6.16 |
| 2012/0053673 | A1 | 3/2012 | Golding et al. |
| 2013/0267883 | A1 | 10/2013 | Medrano |
| 2016/0199562 | A1 | 7/2016 | Parisotto et al. |

FOREIGN PATENT DOCUMENTS

| | | |
|---|---|---|
| JP | 2000-24016 A | 1/2000 |
| JP | 2001-333976 A | 12/2001 |
| JP | 2004-195203 A | 7/2004 |
| JP | 2005-342508 A | 12/2005 |
| JP | 2006-198393 A | 8/2006 |
| JP | 4144647 B1 | 9/2008 |
| JP | 2008-279138 A | 11/2008 |
| JP | 2014-113423 A | 6/2014 |
| JP | 2014-518692 A | 8/2014 |
| JP | 2014-530672 A | 11/2014 |
| JP | 2014-530677 A | 11/2014 |
| JP | 2015-13189 A | 1/2015 |
| JP | 2017-18218 A | 1/2017 |
| JP | 2018-501873 A | 1/2018 |
| WO | WO 2006/116188 A2 | 11/2006 |
| WO | WO 2007/061100 A1 | 5/2007 |
| WO | WO 2012/148790 A1 | 11/2012 |
| WO | WO 2013/044173 A1 | 3/2013 |

OTHER PUBLICATIONS

Ohira, et al., "Urine output after the initiation of dialysis therapy", Journal of Japanese Society for Dialysis Therapy, 23(11), 1275-1279, 1990 (English Abstract).

http://yu-toseki.jp/swfu/d/study8-sp2.pdf, Brief Explanation: This article describes a method of controlling water removal in hemodialysis and advantages thereof (Translation of p. 5).

Miyagawa, et al., "Study of Usefulness of Laser Blood Flowmeter," http://www.tokyo-hd.org/pdf/44th/44th_04_18.pdf (Partial translation)(Translation from the first page, the first line to p. 2, line 3.).

Taniguchi, et al. "The development of intravenous catheter with percutaneous device made of sintered hydroxyapatite", Japanese Journal of Artificial Organs, 19(3), 1202-1205, 1990 (English Abstact).

* cited by examiner

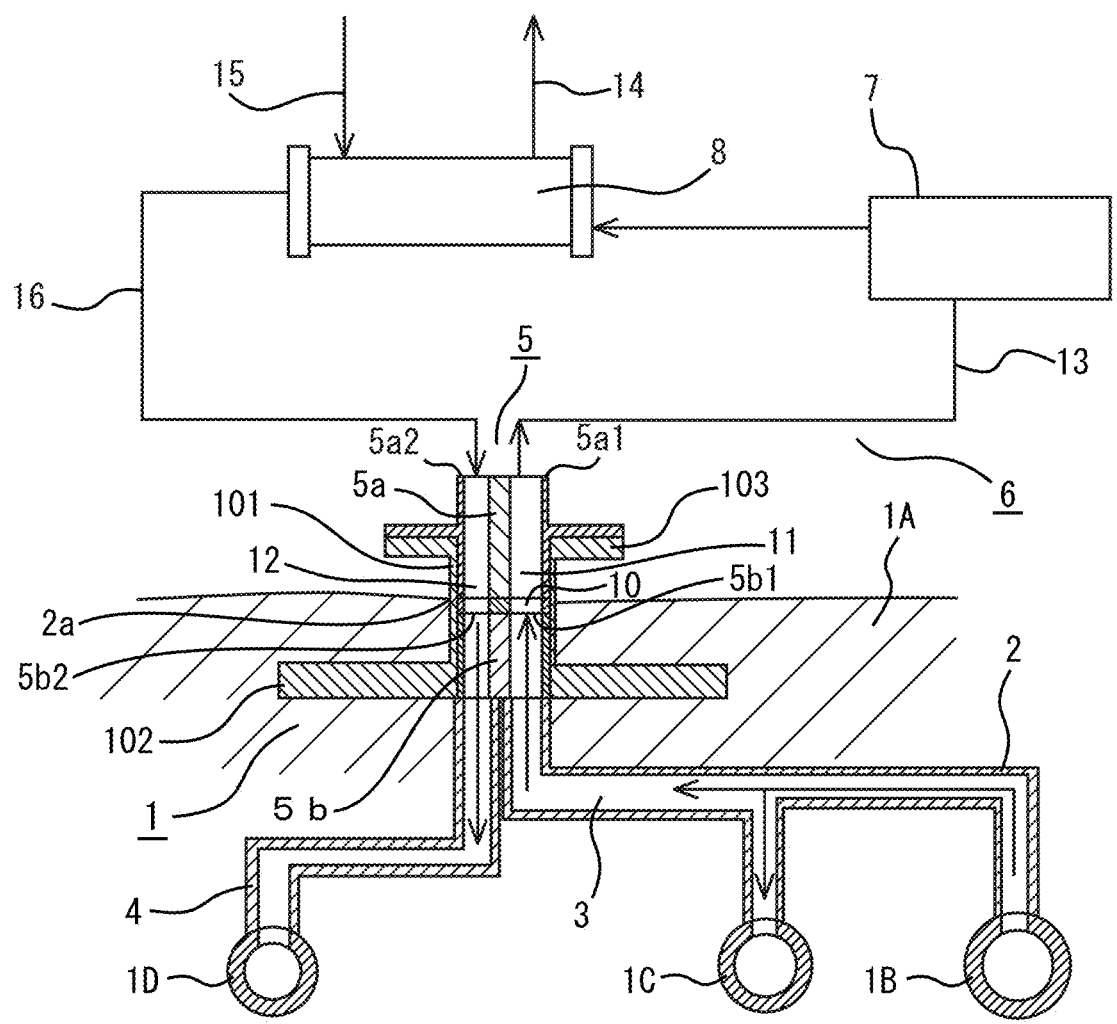

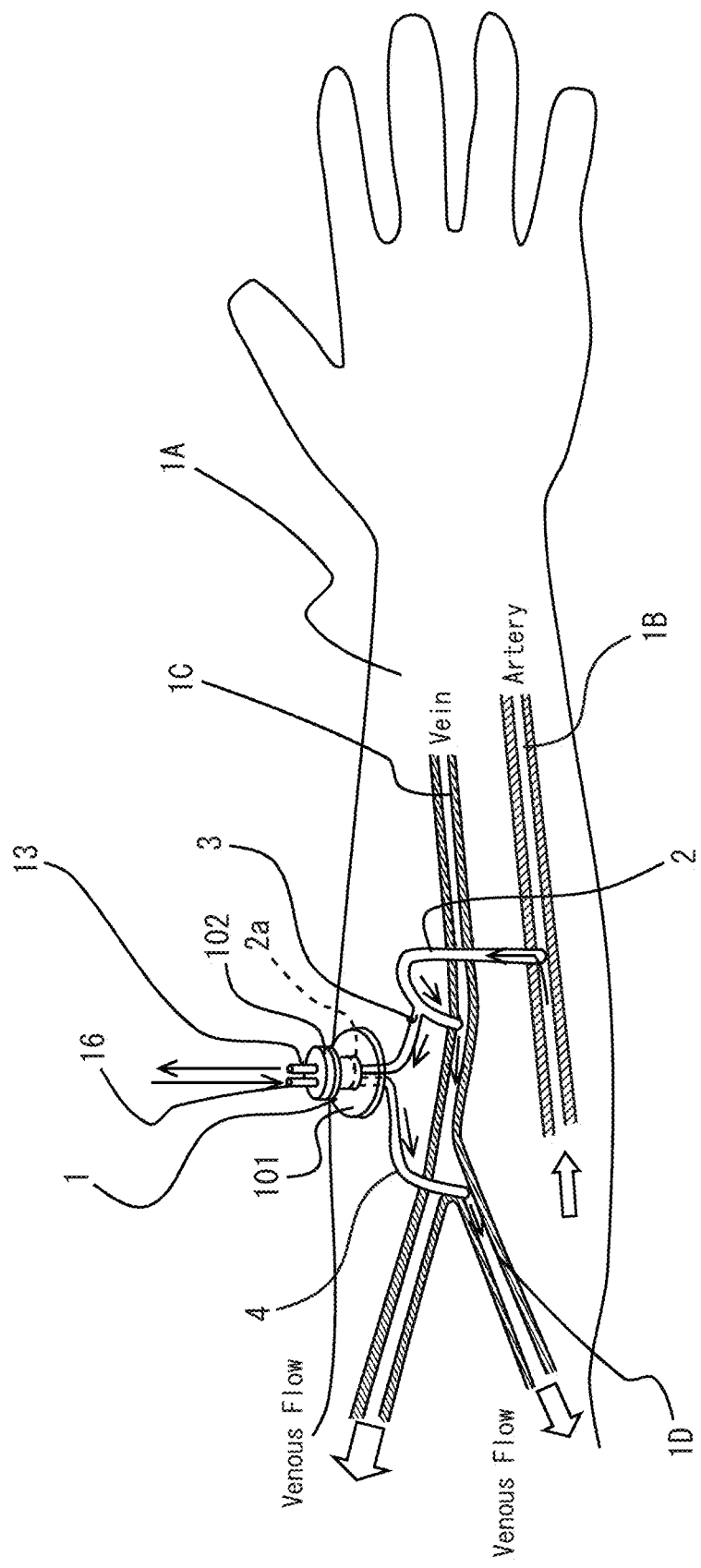

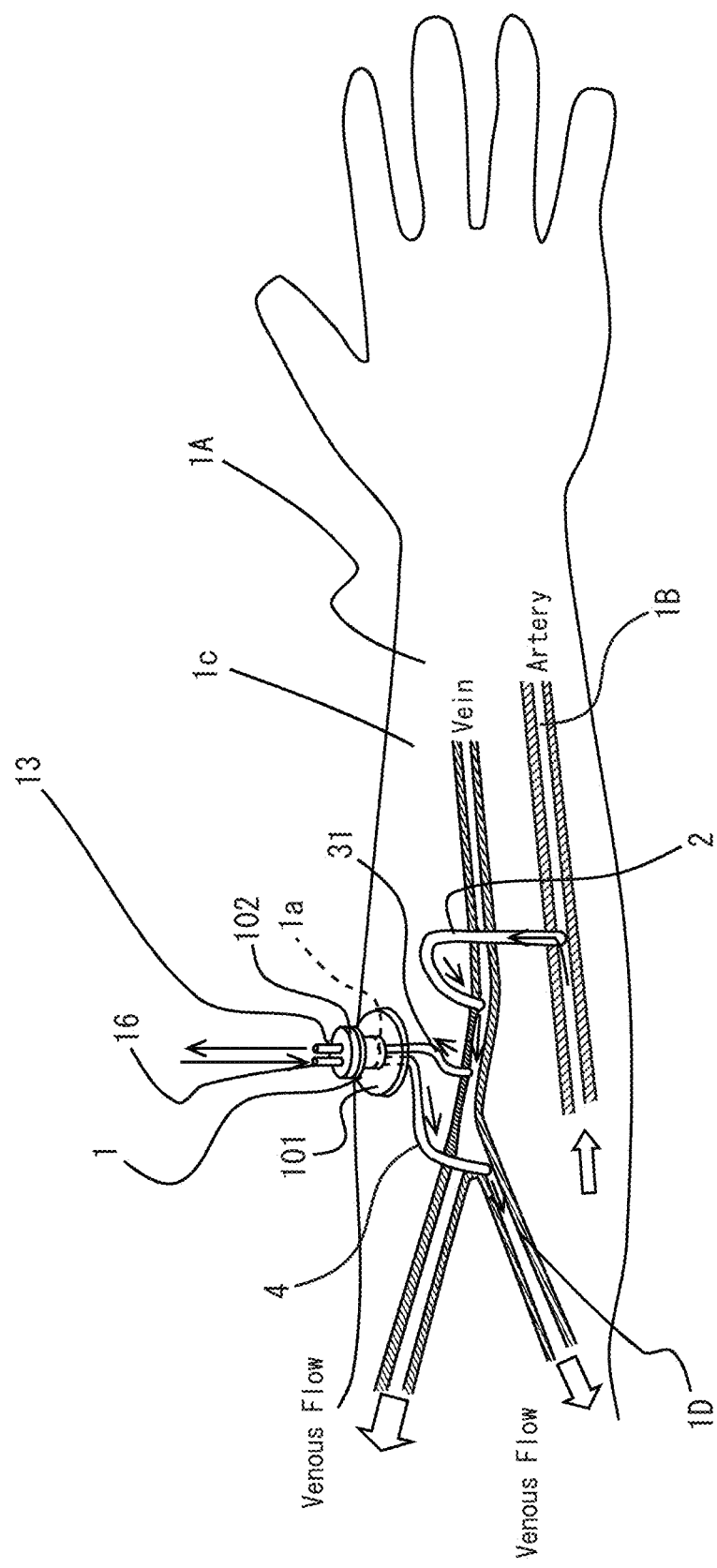

```
def main():
    zzz=1
    lax=[];lay=[];lbx=[];lby=[];lcx=[];lcy=[]
    try:
        while zzz < 26:
            # read csv
            zzx=str(zzz);fr=0
            fa="/home/pi/aidd/"+zzx+".csv"
            zp=''
            while True:
                if os.path.exists(fa):
                    za=zzz*100;zaa,zab =divmod(za,60);print(za,zaa,zab)
                    break
                time.sleep(0.5)
            users = np.genfromtxt(fa, dtype=None,delimiter=",")
            users_r = users
            # clustering by K-means
            model = KMeans(n_clusters=3,max_iter=300).fit(users)
            modela=model.fit_transform(users)
            # plot the result on a scatter diagram
            zza = zzz*0.3
            for (i, label) in enumerate(model.labels_):
                if label == 0:
                    plt.scatter(users_r[i, 0], users_r[i, 1],c='red', label='cls_A')
```

FIG. 15B

```
elif label == 1:
    plt.scatter(users_r[i, 0], users_r[i, 1],c='black',label='cls_B')
elif label == 2:
    plt.scatter(users_r[i, 0], users_r[i, 1],c='blue',label='cls_C')
# draw centroids (centers) of cluster
centers = model.cluster_centers_
plt.scatter(centers[:, 0], centers[:, 1],s=100,c="pink",facecolors='none', edgecolors='red')
cta=centers
cxa=round(cta[0,0],3)
cya=round(cta[0,1],3)
cxb=round(cta[1,0],3)
cyb=round(cta[1,1],3)
cxc=round(cta[2,0],3)
cyc=round(cta[2,1],3)
# distance between centers
caa=(cxa,cya) ;cab=(cxb,cyb) ;cac=(cxc,cyc)
lax.append(cxa) ;lay.append(cya) ;lbx.append(cxb) ;lby.append(cyb) ;lcx.append(cxc) ;lcy.append(cyc)
# modification of centroids
plt.title(zzx)
plt.grid()
file_b = "/home/pi/aidd/"+zzx+".jpg"
plt.savefig(file_b)
```

PERCUTANEOUS TERMINAL FOR HEMODIALYSIS AND INDIVIDUALIZED HEMODIALYSIS SYSTEM

CROSS-REFERENCE TO RELATED APPLICATION(S)

This application is a U.S. National Phase Patent Application and claims priority to and the benefit of International Application Number PCT/JP2019/026194, filed on Jul. 1, 2019, which claims priority of Japanese Patent Application Number 2018-124023, filed on Jun. 29, 2018, the entire contents of all of which are incorporated herein by reference.

FIELD

The present invention relates to a percutaneous device for communicating between inside and outside a living body using a conduit during hemodialysis, and an individualized hemodialysis system which enables shortening of a dialysis time per dialysis treatment with less frequent dialysis treatments, such as once a week.

BACKGROUND

Conventionally, hemodialysis requires the circulation of a large volume of blood, approximately 200 ml per minute, to form a blood circuit in which the blood of a patient with renal failure is taken outside, filtered through a dialyzer, and then returned to the patient. It is impossible to take such a large amount of blood out of the body using only a vein. Therefore, in order to utilize the blood flow of an artery, an artery and a vein are connected via an artificial blood vessel or an operation is performed to directly connect an artery and a vein to draw blood from a nearby vein, and the blood filtered through a dialyzer is returned to the vein (internal shunt).

During dialysis, two hollow puncture-type conduits (needles) are inserted into the blood vessel near the artery near the internal shunt and into the nearby vein to input and output blood. However, it is very painful for the patient to puncture from the skin surface to the blood vessels, and the puncture of the puncture-type conduit hardens or damages the skin, making it impossible to use the internal shunt, or an infection occurs at the damaged portion by puncturing, and it is necessary to perform surgery such as reposition of the internal shunt, which causes much more pain to the patient. Further, since a large amount of blood circulates in the blood circuit, leakage of blood to the outside is often a serious accident, and the accident of needle removal during hemodialysis treatment is the most common accident.

Therefore, it has been proposed to indwell a percutaneous device having biocompatibility on a living skin and to form a dialysate conduit for peritoneal dialysis via the percutaneous device, using a percutaneous device formed of hydroxyapatite, as disclosed in, for example, Japanese Unexamined Patent Publication No. 2000-24016. In addition, it has been reported that the proposed percutaneous device can enable long-term indwelling by binding to skin tissue in a manner that it extends over the inside and outside a living body.

In WO 2007/61100 A1, a hydroxyapatite composite particle or the like made into a short fiber is used as a percutaneous device.

Artificial blood vessels have also been put to practical use, and have been used for shunt formation during hemodialysis treatment.

Japanese Patent Publication No. 4144647 discloses a configuration in which a puncture needle has a concentric two-layer structure with an outer periphery for blood removal and an inner periphery for blood return.

Japanese Unexamined Patent Publication No. 2008-279138 discloses a device using titanium and a metal nonwoven fabric as a percutaneous device used to connect an organ in a living body or an artificial organ to an external device.

As described above, the use of an internal shunt is one factor that can cause pain to the patient, but there are various other factors as well. For example, hemodialysis treatments that have been performed for patients with chronic renal failure are mostly a uniform treatment in which blood is circulated through an extracorporeal dialyzer (filter) for four hours, three times a week, to remove water and wastes such as creatinine and uremic toxins using the uniform water removal method. In other words, six punctures are required for dialysis treatment three times a week, which must be continued for the rest of the patient's life. In addition, patients need to get used to the drop in blood pressure and the instability of blood pressure, and some patients may even die from refusal of dialysis treatment. The commonly used uniform water removal methods removes water at a constant rate, which means that excess water distributed throughout the body over 48 to 72 hours is removed from the body (from the blood vessels) in a short period of time. Furthermore, since the water that can be directly manipulated by dialysis treatment is limited to that present in the blood vessels, there is a risk of causing dehydration in the blood vessels and a drop in blood pressure.

Also, it has been pointed out that, once hemodialysis treatment begins, there is no possibility of utilizing the residual renal function, leading to anuria. Although the degree of maintenance of the residual renal function varies depending on the individual difference of patients, patients become almost anuric within about six years and the possibility of residual renal function (Non-Patent Document 2: "Urine output after the initiation of dialysis therapy", Journal of Japanese Society for Dialysis Therapy, 1990, 23(11), 1275-1279).

Japanese Unexamined Patent Publication No. 2014-113423 discloses attaching a perspiration sensor body to a patient, and then starting measurement by a perspiration amount measuring means. It also discloses that the amount of perspiration on the patient's forehead is constantly monitored, and when an abnormality in the amount of perspiration is detected, a non-invasive blood pressure monitor is activated to confirm the abnormality, thereby detecting a drop in blood pressure at an early stage and implementing a recovery treatment.

Japanese Unexamined Patent Publication No. 2014-530672 discloses that since the posture of a patient affects the amount of plasma, the posture of the patient is determined in advance, and at least one of setting, controlling and adjusting of the water removal rate (an amount of water removal per unit time) is performed in accordance with the determined posture of the patient.

Japanese Unexamined Patent Publication No. 2015-13189 discloses storing treatment information relating to the patient's hemodialysis treatment and notification information representing an alarm or a precaution to be informed under predetermined conditions during hemodialysis treatment in association with each other for each patient. The information during the hemodialysis treatment of a patient is compared with the stored treatment information, and when it is determined that an alarm or caution is necessary, the patient's notification information is displayed as text data on the information display section of the hemodialysis apparatus. When the content of the notification of the abnormality and the notification content of the precautions differ for each patient, the content of the notification according to the patient is accurately notified to the medical staff.

Japanese Unexamined Patent Publication No. 2018-501873 discloses a step of receiving patient's evaluation information relating to one or more personal characteristics of a patient, a step of determining a patient evaluation score based on the received patient evaluation information, and a step of modifying the operation of a medical fluid treatment machine based on the patient evaluation score.

Japanese Unexamined Patent Publication No. 2014-518692 discloses devices, systems, and uses for monitoring patient parameters and blood fluid removal system parameters and identifying the system parameters that result in improved (more effective) or worsened (less effective) patient parameters.

PRIOR ART DOCUMENTS

Patent Documents

Patent Document 1: Japanese Patent Publication No. 4144647
Patent Document 2: International Publication WO 2007/61100 A1
Patent Document 3: Japanese Unexamined Patent Publication No. 2000-24016
Patent Document 4: Japanese Unexamined Patent Publication No. 2008-279138
Patent Document 5: Japanese Unexamined Patent Publication No. 2014-113423
Patent Document 6: Japanese Unexamined Patent Publication No. 2014-530672
Patent Document 7: Japanese Unexamined Patent Publication No. 2015-13189
Patent Document 8: Japanese Unexamined Patent Publication No. 2018-501873
Patent Document 9: Japanese Unexamined Patent Publication No. 2014-518692

Non-Patent Documents

Non-Patent Document 1: "Study of Variations in Circulation Blood Volume and Automated Control of Ultrafiltration Rate Using a New Monitoring System During Hemodialysis", Japanese Journal of Artificial Organs, 28(2), 339-334, 1999
Non-Patent Document 2: "Urine output after the initiation of dialysis therapy", Journal of Japanese Society for Dialysis Therapy, 1990, 23(11), 1275-1279
Non-Patent Document 3: http://yu-toseki.jp/swfu/d/study8-sp2.pdf
Non-Patent Document 4: "Initiation of Once-A-Week Hemodialysis", Japanese Journal of Rural Medicine, 2002, 51(2), 68-73
Non-Patent Document 5: http://www.tokyo-hd.org/pdf/44th/44th_04_18.pdf

SUMMARY

Technical Problem

As described above, hemodialysis treatment is painful because two puncture needles are used to puncture veins. Accordingly, there is a need for a way to avoid puncturing each time.

Although the use of a percutaneous device is also considered, simply by the presence of a biocompatible component placed inside and outside the skin, there are many unexplained points in using a percutaneous device in hemodialysis which uses the vigorous venous blood flow (virtually, an arterial flow) connected to an artery. Further, if the inside of the percutaneous device has a complicated detachable configuration, infection from the inside of the percutaneous device which penetrates the inside and outside the living body may occur.

Also, in hemodialysis treatment, an attempt to predict a decrease in blood pressure from the patient's perspiration amount as disclosed in Japanese Unexamined Patent Publication No. 2014-113423, or an attempt to set the amount of water removal based on the patient's posture as disclosed in Japanese Unexamined Patent Publication No. 2014-530672. However, due to the individual differences among patients, it has not always been possible to adequately predict the prevention of a decrease in blood pressure.

Adjusting the amount of water removal by paying attention to the PRR value and performing slow water removal are now being implemented in dialysis institutes by operating a dialysis apparatus, as described in the above-mentioned documents. However, the determination of the relationship between the PRR value and the amount of water removal is based on manual setting based on the medical insights of doctors, clinical technicians, and nurses, and the BV meter can only provide information on extracorporeal blood volume. Accordingly, there are many unexplained points about the configuration for automatic adjustment in consideration of individual differences of patients while considering the state of blood vessels in the body, etc.

Solution to Problem

The present invention eliminates the patient's pain caused by punctures and realizes the formation of a blood removal path and a blood return path that are easier to install by a percutaneous device comprising: a contact body comprising a biocompatible member which is to be contacted with a skin tissue at inside and outside a living body; a tubular body having one end which is to be connected to an artery and an another end which is to be connected to a vein; a blood removal tubular body for supplying blood to an external blood circuit, one end of the blood removal tubular body is to be connected to a side surface of the tubular body; and a blood return tubular body having one end which is to be connected to a vein and an another end which is to be connected to a blood returning part of the blood circuit; wherein the another ends of the blood removal tubular body and the blood return tubular body are arranged at the center of the contact body. The percutaneous device for hemodialysis according to the present invention can be easily placed at the patient's dialysis site in conjunction with the internal shunt during an internal shunt surgery using a normal artificial blood vessel.

Examples of the contact body in the present invention include a dense body or a porous body of a calcium phosphate ceramics material such as hydroxyapatite, tricalcium phosphate, etc.; or a metal body such as titanium, alumina, etc., having an oxide coating formed on a mirror-polished surface by immersion into a calcium phosphate-containing high concentration solution and pressurized hydrothermal treatment. As a method for manufacturing the contact body (percutaneous device), a known method may be used, and examples thereof include a method in which a hydroxyapatite manufactured by a wet synthesis method is subjected to pressure shaping and then a firing treatment is performed.

As a method for forming an oxide coating forming method, for example, the same method as the method for forming an oxide coating on the contact surface between the artificial teeth root and gum as described in, for example, Japanese Unexamined Patent Publication No. 2014-50610 is suitable.

That is, a percutaneous device core material with a mirror-polished surface is immersed in a solution supersaturated with calcium phosphate, and then is subjected to hydrothermal treatment. Mirror polishing is performed using a method such as mechanical polishing by a polishing paper, a surface buff, roller burnishing, etc., chemical polishing, or electrolytic polishing in order to remove minute surface irregularities. After mirror polishing, the material is immersed in a supersaturated aqueous solution containing phosphoric acid and a calcium component, and is subjected to hydrothermal treatment to form a hydrothermal synthetic coating containing phosphorus and calcium components.

In the hydrothermal synthetic coating treatment, for example, a percutaneous device made of mirror-polished titanium is immersed in an aqueous solution having a pH of 5.5 to 12 in which phosphate and calcium ions coexist and the concentration of phosphoric acid or the like is supersaturated or locally supersaturated for 9 to 28 hours at a temperature of 110° C. to 125° C. and a pressure of 0.1 to 0.2 MPa. The coating to be formed is an oxide coating and may contain at least phosphoric acid and calcium.

Examples of the contact body in the present invention include a cylindrical body with an inner diameter ranging from large enough to insert two or one puncture needles to one or two tubular bodies with an inner diameter of up to about 10 mm. Preferably, a small one is preferred because it can reduce the burden on the patient from the ease of contact body surgery.

Further, in the present invention a connection structure that can be vertically separated can be formed within the percutaneous device that forms the contact body, and the connection structure has an opening and closing part that closes the tubular body at the lower part when the connection structure is vertically separated. This opening and closing part is configured to be closed at least when the connector upper part or the lid part is removed, and to be opened when the upper part of the connector is attached thereto and during use, as illustrated for a hollow body for puncturing in FIG. 4. Further, since the opening and closing part should prevent the release of blood from the hollow section for the blood returning part during use, the opening and closing part may not be required if a pressurized space is formed and replaced.

Percutaneous Device

The percutaneous device can be manufactured by 3D printing a synthetic apatite powder produced by wet-synthesis using a 3D printer. After molding, the surface which is to be contacted with the skin is finished into a mirror surface without irregularities. The molding method is not limited to the 3D printer, and may be a conventionally used molding method such as injection molding. However, when a control function is operated inside, a 3D printer having flexibility in molding is preferable. Further, the molding may be performed by pressure molding or injection molding the outside followed by firing, and subjecting the inside to a 3D printer. Since the part which comes into contact with the skin tissue preferably has a mirror surface, it is preferable that the surface is mirror-polished after molding. However, depending on the type of 3D printer, when a mold is used, the corresponding surface may become a mirror surface, and in such a case, a polishing process is not required.

Further, in the present invention, hemodialysis is performed through a percutaneous device, which serves as an entrance and exit point provided in the percutaneous, instead of using a conventional puncture needle, thereby increasing the possibility of expanding the degree of freedom other than going to a specialized medical institution beyond visiting specialized medical institutions, such as the freedom of home treatment, long-distance treatment, etc. On the other hand, when urine components are removed from blood vessels, the amount of blood is manipulated, which increases the possibility of occurring a blood pressure drop and fluctuations, and other complications, and therefore there is a greater need for blood pressure stability with hemodialysis treatment.

Thus, in another embodiment, the present invention provides an individualized hemodialysis apparatus comprising:
  an intracorporeal information detection unit for measuring an intracorporeal blood flow volume and blood pressure-related information; and
  a storage means in which a program for executing the following steps is stored:
    a step of detecting baseline information from the intracorporeal blood flow volume obtained by the intracorporeal information detection unit;
    a step of detecting variations in blood flow baseline and variations in blood pressure by detecting variations per unit time in the baseline information and the blood pressure-related information;
    a step of detecting a two-dimensional variation from the variations in blood flow baseline and the variation in blood pressure;
    a step of forming two-dimensional variation data by detecting a predetermined number of two-dimensional variations;
    a distribution range forming step in which a predetermined number of distribution ranges is formed for the distribution state of the two-dimensional variation data;
    a step of forming a characteristic point of each range obtained in the distribution range forming step; and
    a step of detecting a blood vessel condition in which the blood vessel condition is detected from the characteristic point and the distribution range.

By using a method of hemodialysis based on individual differences using the individualized hemodialysis device, the patient's blood vessel condition at the time of dialysis treatment is understood, thereby stabilizing blood pressure and realizing dialysis treatment in a state more similar to that of one's own kidney.

In another embodiment of the individualized hemodialysis apparatus of the present invention, a program for executing the following steps is further stored in the storage means:
  a step of selecting a water removal pattern according to individual differences;
  a step of collecting blood information while performing water removal according to the water removal pattern;
  a step of calculating an intravascular immersed body fluid volume from the blood information; and
  a step of increasing a water removal rate in which, when the intravascular immersed body fluid volume is decreased beyond a predetermined rate, the water removal rate is allowed to be decreased, and when the intravascular immersed body fluid volume is increased beyond a predetermined rate, the water removal rate is allowed to be increased.

Also, at the time of dialysis treatment, the blood volume in a blood vessel condition is obtained by combining the external blood-related volume detection step of obtaining the external blood-related volume, and water removal state information is measured. By obtaining these sufficient water removal and uremic toxin excretion from vascular information and water removal state information, effective maintenance of residual renal function can be performed for patients with partially effective residual renal function (RRF).

Further, the present invention includes a step of setting a high water removal rate at the start of dialysis, and a step of adjusting a water removal rate based on blood flow baseline information and blood pressure-related information from the start of dialysis and two-dimensional variation data obtained from these information, thereby performing removal of a large amount of water from the start of dialysis until before the body's reaction due to water removal occurs, and consequently realizing sufficient water removal while maintaining a stable blood pressure and physical and mental state within a predetermined time.

The setting of the water removal rate pattern in the present invention refers to, for example, time-series variations shown in FIGS. 19B to 19D. FIG. 19B shows uniform water removal in which water is removed at a constant rate, and shows a currently common treatment method. Also in the present invention, it can be shown as one example of the pattern, but the patterns shown in FIGS. 19C and 19D are preferably used, and other patterns may be set according to individual differences.

For example, the water removal pattern and the dialysis treatment time may be determined by measuring serum creatinine level, estimated glomerular filtration rate (eGFR), and urine volume in advance to confirm the residual kidney amount, or the water removal pattern is determined by confirming the patient's condition (body temperature, physical condition, blood pressure value, etc.) at the time of treatment. The predictive determination of the threshold values for the variations in the water removal pattern and the PRR value may be set in a predictive manner by a machine learning process such as random forest, based on the patient's data, the evaluation data after the previous dialysis treatment, etc.

The blood pressure-related information in the present invention is preferably a BV (blood volume) meter for measuring a blood volume obtained by calculating mainly a PRR value (plasma refilling rate) as an extracorporeal measurement item, and a laser blood flowmeter, a sphygmomanometer, and a PWTT blood pressure-related measurement device can also be used as intracorporeal measurement items.

The water removal control in the present invention refers to performing an operation in which, with respect to variations in blood pressure-related information, for example, variations in the PRR value obtained as described above, when it falls below a certain threshold, the water removal is judged as excessive, and the water removal rate is lowered, and conversely when it exceeds a certain threshold value, the water removal rate is increased to increase the water removal amount. At this time, the intracorporeal blood flow volume and blood pressure value are measured, and the threshold values thereof differ depending on the patient. In this case, since the PRR value obtained from the extracorporeal blood volume does not include the intracorporeal blood vessel information, it is preferable to adjust the water removal amount, etc., based on the combination of the PRR value obtained from the extracorporeal blood volume and the blood vessel information obtained based on the intracorporeal blood flow information and the blood pressure information.

The blood driving means in the present invention is used in existing dialysis apparatuses, and represents, for example, a blood pump for circulating 200 ml of blood per minute to a blood circuit formed outside the body. The blood driving means is a means for ensuring the necessary blood flow rate for drawing blood from the blood access near a shunt part and for flowing the blood into the blood circuit.

The blood filtration unit is a hollow fiber filter (dialyzer), which is a bundle of multiple filamentous hollow fibers formed of a hemodialysis membrane (porous membrane) such as a PS membrane, a PES membrane, a PEPA membrane, a PMMA membrane, an EVAL membrane, and a PAN membrane, etc., and has a function of discharging waste and moisture by utilizing the difference in the concentration of the dialysate flowing around and the blood flowing inside.

The water removal adjustment means in the present invention discharges the water permeated and conveyed from the dialysis machine together with the dialysate, and includes a configuration in which the discharge is adjusted at least by an external signal of an electromagnetic valve, etc.

The blood measurement means is comprised of a BV meter for measuring blood flow (blood volume) outside the body, a hematocrit value monitor, a laser blood flowmeter for measuring intracorporeal blood flow, a sphygmomanometer, a PWTT measuring device, etc., and collect blood information such as blood pressure, intracorporeal blood flow volume, extracorporeal blood volume, etc.

The hematocrit value monitor is one which, for example, utilizes near-infrared spectroscopy, and uses as a sensor a combination of a light emitting diode which outputs near-infrared light and a light receiving semiconductor device which receives the reflected return light from the light emitted by the light emitting diode to the blood tissue, and is attached to the surface of the blood circuit conduit for measurement in a non-contact state against the blood. The hematocrit value monitor may use an existing product.

The BV meter for measuring blood volume having the same function as a hematocrit monitor is a device which is attached to an arterial blood circuit between a dialyzer and a blood removing part, and measures blood volume and total volume variations of red blood cells, etc., and at least a device capable of calculating at least a PRR (plasma refilling rate) value indicating a ratio of a body fluid permeated and supplied from outside the blood vessel into the blood vessel is used.

The laser blood flowmeter is a device that irradiates a laser beam and measures a blood flow rate and a blood flow volume based on the reflected light, and a laser Doppler blood flowmeter or the like is suitably used.

The sphygmomanometer may be either a pressurized type such as an oscillometric method or a non-pressurized type, and a device that can continuously measure for a long time is used.

The blood pressure-related value measurement device is, for example, a PWTT type (a device that measures the rise and fall of blood pressure based on a distance value between a R wave of the electrocardiogram and the rise of a pulse wave).

According to the present invention, the water removal operation based on the blood vessel condition is enabled by obtaining multidimensional data representing the transition of the blood vessel condition from the blood pressure variation and the blood flow baseline variation.

The present invention ensures an effective water removal amount by storing an initial water removal pattern in advance, selecting an initial water removal pattern based on the patient's individual differences, performing water removal based on the variation according to the water removal pattern, and obtaining the blood vessel condition information based on the blood flow baseline information and blood pressure-related information to adjust the water removal amount.

The initial water removal pattern is designed to set the initial water removal rate higher than the rate of typical uniform water removal rate (FIG. 19B), and then adjust the rate downward in an enveloping manner at a predetermined slope, as shown in, for example, FIGS. 19C and 19D, and the selection is made according to the patient's individual differences. The rate variation of the pattern is preferably set based on multidimensional information obtained from the intracorporeal blood flow volume and the blood pressure variation.

Although the intracorporeal blood flow gradually decreases due to water removal, it is thought that the timing of a relatively large decrease exists between about 30 minutes and 1 hour after the start of water removal. At the start of dialysis, a treatment is given for a predetermined period of time in which the amount of water removed is relatively large. Before water removal, variation in intravascular volume is considered to be a defensive measure to protect the heart, but in the case of water removal, since the blood volume decreases even in the state of variation in intravascular volume, it is considered that there will be a limit to contraction, and when the limit is exceeded, contraction will be released, resulting in a temporary state of dehydration and a decrease in ABV, which is thought to cause a drop in blood pressure. The selection according to the patient's individual differences is exemplified by the dialysis history, constitution, condition of the patient, etc.

In FIG. 19A, the vertical axis represents BV (blood volume) and the horizontal axis represents time. In the case of uniform water removal, the blood volume decreases at a constant slope.

The present invention comprises a step of selecting a water removal pattern according to individual differences; a step of collecting blood information while performing water removal according to the water removal pattern; a step of calculating an intravascular immersed body fluid volume, PRR value, etc., from the blood information outside the living body; and a step of increasing a water removal rate in which, when the intravascular immersed body fluid volume is decreased beyond a predetermined rate, the water removal rate is lowered, and when the intravascular immersed body fluid volume is increased beyond a predetermined rate, the water removal rate is increased.

The measurement of the intravascular immersed body fluid volume is calculated by a known method based on the blood volume obtained from an extracorporeal blood volume measurement unit such as a BV meter. Further, the calculation may be performed based on blood flow data obtained by a laser blood flowmeter and the fact that the amount of red blood cells in the blood circuit is constant. Further, the present invention performs selection of a water removal pattern, adjustment of a water removal rate, etc., while predicting variations in blood pressure.

Artificial intelligence also includes machine learning such as boosting, clustering, Q-learning, SERSA, and reinforcement learning such as Monte Carlo method, neural networks, random forests, SVM, etc. Alternatively, DQN, which is a combination of neural network (deep learning) and reinforcement learning, may be used.

In the case of reinforcement learning, behavior evaluation data including a reward list is formed. However, this table-like data may be used as a default table for treatment of new dialysis patients, for example, by a DQN that is done in a predictive manner. Also, a combination of multiple machine learning methods or a combination of neural networks may be used to achieve a target blood pressure fluctuation prediction and stabilize the blood pressure based on the prediction.

Effects of the Invention

Only by performing a treatment at the time of internal shunt treatment for hemodialysis with a combination of a percutaneous device and an artificial blood vessel, the present invention eliminates the pain of puncture due to hemodialysis, and enables dialysis treatment without deterioration of veins due to puncture or burden or pain to the patient. Further, by forming a percutaneous device with an inner diameter that is about the same as two diameters of the normally used puncture-type hollow body for vein, implantation surgery becomes relatively easy, and the burden on the patient is reduced, making it possible to set the time of transition to hemodialysis at a time when there is a possibility of maintaining or even recovering residual renal function. Since the arterial flow rate can be adjusted, it is possible to respond to shunt complications that occur when blood is taken out of the artery and needle extraction accidents.

Further, hemodialysis treatment, which no longer requires puncture, provides an increased degree of freedom at home, which enables tailor-made hemodialysis treatment by adjusting the amount of water removal based on blood pressure fluctuations, etc., during hemodialysis treatment, and individual difference information such as blood flow data, blood pressure data, circulating blood volume, etc., and consequently making it possible to provide dialysis treatment at a place other than specialized medical institutions, at home, etc.

Moreover, the present invention realizes dialysis treatment that makes use of the residual renal function, with stable blood pressure by increasing or decreasing the water removal amount for each individual difference, and dialysis treatment only once a week, with urine components discharged by self-urination on other days.

BRIEF DESCRIPTION OF DRAWINGS

FIGS. 1A and 1B are diagrams showing an embodiment of the present invention.

FIG. 2 is a diagram for illustrating one embodiment of the present invention.

FIG. 3 is a diagram for illustrating one embodiment of the present invention.

FIGS. 15A and 15B are diagrams for illustrating another embodiment of the present invention.

DESCRIPTION OF EMBODIMENTS

Figure 1B:
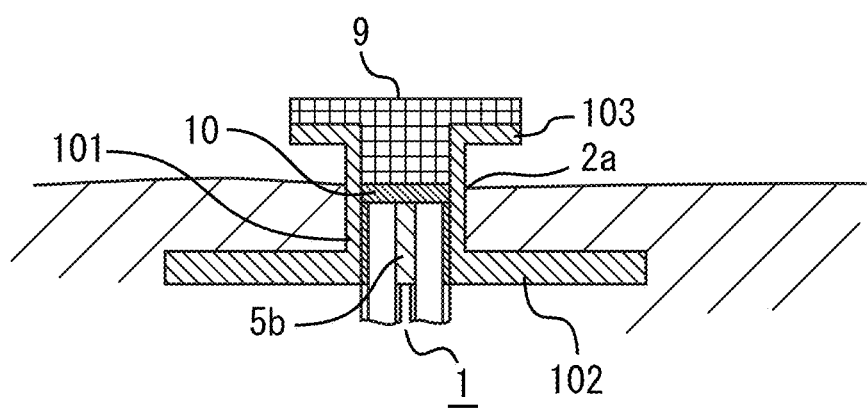

The present invention has a configuration in which at least a contact body (transcutaneous terminal) with a biocompatible member placed at a skin contact part connecting inside and outside of a living body, a tubular body for forming a blood removing part, and a tubular body for forming a blood returning part have a connector state that can be joined and detached at the terminal.

The contact body is formed at least at a site communicating between the inside and outside of a living body, and examples thereof include a molded dense body of a biocompatible member such as calcium phosphate ceramics including hydroxyapatite, calcium deficient hydroxyapatite, α-type and β-type tricalcium phosphate, alumina ceramics, etc., obtained by wet synthesis, bone powder extraction, etc., and those having an oxide coating by mirror-polishing a surface of a titanium core material, immersing it in a supersaturated aqueous solution containing a phosphate and calcium salt, and subjecting it to a hydrothermal treatment with heat and pressure.

The shape of the percutaneous device is not particularly specified, but a smaller and more stable shape is preferable. By reducing the size, the operation can be simplified and the burden on the patient can be reduced.

The contact body is, for example, in the form of a cylindrical shape or a bobbin shape in which the diameter of the edge of the bottom part is wider than the upper part, and a connector is arranged at the center of the contact body to form a connector capable of separating a tubular body communicating inside and outside the living body, and has a configuration which, for example, adds resistance to the flow from an artery or blocks the venous and arterial flows, thereby enabling reduction of shunt complications, for example. In particular, by forming a configuration capable of controlling the arterial flow inside the connector, it is also possible to reduce the load on the venous flow.

The tubular body should at least have biocompatibility and can be used as an artificial blood vessel, and may be any one that is usually used to form an internal shunt.

In addition, the present invention enables the blood removing part and the blood returning part to be detachably configured inside the contact body with the skin, and the blood removing part and the blood returning part are puncture hollow needles in the same manner as before. The present invention may have a configuration which enables adjustment of the blood flow volume from an artery to a vein from the outside by simply encapsulating the middle of the artificial blood vessel which connects an artery and a vein when the artificial blood vessel is used as an internal shunt in the contact body, and forming a configuration in which the tubular side of this encapsulated artificial blood vessel is pressured from the outside.

This makes it possible to reduce the shunt complications in the veins by making it possible to optionally adjust the vigorous blood flow like arterial flow from the outside, and actually enables internal shunting only during dialysis treatment. In this case, since the operation from the outside is only to press the side surface of the tubular body within the contact body, the inside and outside the living body can be completely shut off, thereby enabling steady use of the percutaneous device.

That is, it comprises a contact body made of a biocompatible material which is to be contacted with a skin tissue at inside and outside a living body, a tubular body which passes through the inside of the contact body, an operation driving part which is placed inside the contact body and can form a blocked state by manipulating the side surface of the tubular body, and an operation part which enables manipulation of the operation driving part at a surface of the contact body external to the living body.

The contact body is not a cylinder as described above, but is, for example, a columnar body, a rectangular body, etc., and a part thereof is embedded in the skin so that a part of it is exposed on the skin surface. A tubular body such as an artificial blood vessel, which is installed without being exposed to the outside of the living body, passes through the interior of the contact body, and in the middle thereof, an operation driving part for closing the interior of the tubular body by a pressure from the outside is formed. A configuration for pressing the side surface of the tubular body is formed inside the contact body, and an operation part for forming this pressure is incorporated into the upper part of the contact body, which is to be exposed to the outside of the body, thereby enabling operation from the outside. This configuration makes it possible to adjust the flow of arterial flow without connecting the inside and outside of the living body, thus reducing shunt complications.

The present invention has a configuration in which a percutaneous device made of a calcium phosphate dense body such as hydroxyapatite is implanted into the skin, a blood removing part is formed by an artificial blood vessel from the vicinity of a shunt part connecting an artery and a vein with an artificial blood vessel, and a blood returning part is formed by an artificial blood vessel for returning the blood purified by a dialysis apparatus to the body, thereby returning the blood to the body via the percutaneous device. That is, if the blood returning part and blood removing part of the percutaneous device are sockets, they can be connected by an external blood conduit in the form of plug to form a blood circuit during dialysis treatment. This will broaden the scope of home hemodialysis treatment, which until now has been limited by the need for puncture, an action that can only be performed by a doctor or other medical professional or the patient, and furthermore, it is possible for patients to receive, for example, one to two hours of dialysis treatment every day. For a daily dialysis menu of one to two hours, although the variations in blood vessel volume differ depending on individual patients, the decrease in blood flow and the decrease in blood pressure are linked with each other for the first 30 minutes to an hour after the start of dialysis treatment, and even with uniform water removal, it is possible to conduct a relatively gentle dialysis treatment. Accordingly, if there is a lot of water in the blood vessels, the amount of water removal is initially set higher to remove wastes such as uremic toxins and water, thereby enabling a dialysis treatment which can be performed at the patient's pace.

After the start of dialysis treatment, in the case of uniform water removal, there is a timing at which blood pressure rises in response to a decrease in blood flow in 30 minutes to 1 hour, but this timing is considered to be the timing of vasoconstriction, and after that, the blood flow volume decreases, becoming a state of low blood flow. The state of vasoconstriction is also understood as a defensive action for the heart, and occurs when water is removed from the blood in the vessels to some extent.

Incidentally, once vasoconstriction occurs, it takes time for the contraction to be released. Therefore, a program which stops water removal before the timing of this constriction and starts water removal again at the timing when the blood flow rate increases is created and executed.

According to the present invention, by varying the rate of water removal in a pattern according to individual patient differences and controlling the rate of water removal based on blood information, sudden hypotension and fluctuations in blood pressure can be suppressed, and thereby enabling elimination of headaches, leg cramps and hypothymia, and thus improving life prognosis, etc. As a result, the present invention provides stable hemodialysis treatment with sufficient water removal and uremic toxin elimination. For hemodialysis patients with residual renal function, a state that allows for recovery of renal function is formed, and sufficient treatment can be provided by weekly hemodialysis treatment as described in "Initiation of Once-A-Week Hemodialysis", Japanese Journal of Rural Medicine, July 2002, 51(2), 68-73".

Variations in intravascular volume are necessary for defending the body during blood outflow, but during water removal, an excessive water removal rate may cause intravascular dehydration even if the water removal is not sufficient.

The detection of variation in intravascular volume is exemplified by the detection of the relationship between blood flow and blood pressure with a combination of a blood flowmeter and a sphygmomanometer for measuring the intracorporeal blood flow. However, even if variations in both blood flow and pressure are observed separately, it is difficult to capture the variations phenomenologically. Accordingly, machine learning, and the like, are suitable, among which an unsupervised learning called clustering, such as clustering for the timing of vasoconstriction with multidimensional input, is exemplified.

However, since blood flow is greatly affected by the contraction of muscles around blood vessels due to sympathetic nerves and varies significantly due to stimulation of the skin, it is difficult to capture the waveform as it is. Therefore, based on the assumption about the frequency component that blood flow decreases with a slope corresponding to the rate of water removal, it is preferable to use the minimum points where the downward variation in blood flow turns into an upward variation, or the maximum points where the upward variation turns into a downward variation, and the baseline data obtained by connecting and the midpoint between the minimum points, as the blood flow data.

For the blood flow baseline data, the point where the slope of the blood flow turns from descent to ascent is detected, as described above, and values are obtained by sampling the stored curve obtained by storing the points of variation as a straight line or curve. If the coordinates of the points of variation can be detected, the sample coordinates between these points can be automatically obtained, so it just need to find the coordinates of the points of variation.

The blood pressure-related information is exemplified by the variations in blood pressure obtained by detecting the time width between the time phase of a R wave of the electrocardiogram and the rise time phase of a pulse wave detected at the upper arm, the lower arm, etc., the time width between the rise time phase of a pulse wave at a deep part of a living body and the rise time phase of a pulse wave at a superficial part of the living body, and the time width between the rise time phase of a pulse wave at the heart and a pulse wave of the upper arm, and capturing the variations of these time widths (pulse wave propagation velocity).

In particular, variations in intravascular volume are greatly affected by the sympathetic nerve, and thus are greatly affected by the mental. Patients who want to avoid dialysis, such as dialysis phobia, may have constant changes in intravascular volume due to tension and fear. Therefore, when measuring blood flow in the body, only a small amount of blood flow may be measured due to changes in intravascular volume. In this case, variations in blood flow and blood pressure in the body may form a completely different pattern under low blood flow, making it difficult to use them in dialysis treatment. In such a case, it is preferable to form a stable condition before treatment. If the blood flow is low even in a place where it is easy to measure blood flow, such as the earlobe, it is preferable to measure another part of the body (for example, fingernails) to check if there is sufficient blood flow.

In hemodialysis treatment, the dialysis treatment based on the following steps enable a dialysis treatment based on the patient's renal function, for example, once a week:

- a step of selecting a water removal pattern according to individual differences;
- a step of collecting blood information while performing water removal according to the water removal pattern;
- a step of calculating an intravascular immersed body fluid volume, such as a PRR value, from the blood information; and
- a step of increasing a water removal rate in which, when the intravascular immersed body fluid volume is decreased beyond a predetermined rate, the water removal rate is lowered, and when the intravascular immersed body fluid volume is increased beyond a predetermined rate, the water removal rate is increased.

Further, the hemodialysis treatment performed by the steps is a gentle treatment for patients that maximizes the patient's residual renal function, and can sufficiently remove uremic toxins, thus recovering renal function. If the urine volume and other factors are secured to some extent, hemodialysis can be performed once a week.

The use of a transcutaneous terminal will expand the degree of freedom of dialysis treatment and enable patients to realize a dialysis treatment which makes the most of their own renal function through their own efforts. If the amount of water removal calculated from the patient's weight at the time of dialysis treatment one week after the last hemodialysis treatment can be removed in one day of hemodialysis, then hemodialysis treatment once a week is possible. Further, the duration of the hemodialysis treatment should be such that the amount of water removed is sufficient to stabilize the blood pressure and provide a gentle treatment. Therefore, if the frequency of hemodialysis treatment is once a week, there may be a whole day for hemodialysis treatment, but it is meaningful for patients to be able to realize dialysis treatment only on Sunday or Saturday, and patients may wish to have such a dialysis treatment schedule.

EXAMPLES

The percutaneous device of the present invention will be described with reference to FIGS. 1A and 1B. Reference numeral 1 indicates a percutaneous device. Percutaneous device 1 is composed of, for example, a block of calcium phosphate ceramic such as hydroxyapatite, etc., or a titanium material, and a coating layer, etc., such as an apatite oxide coating, etc., formed on the surface thereof. In percutaneous device 1, a disk-shaped cylindrical bottom edge 102 having a long diameter is formed at the bottom part of a cylindrical main body 101, and a disk-shaped cylindrical top edge 103 having a diameter shorter than bottom edge 102 is formed at the top.

Reference numeral 2 indicates an tubular body for internal shunt as an example of the tubular body. An artificial blood vessel formed of a material selected from GORE-TEX®, expanded polytetrafluoroethylene (ePTFE), polyurethane (PU), polyolefin-elastomer-polyester (PEP), etc., can be used as tubular body 2 for internal shunt. Reference numeral 3 indicates a blood removal tubular body. Blood removal tubular body 3 may be made of the same material as the artificial blood vessel. Reference numeral 4 indicates a blood return tubular body. Blood return tubular body 4 may be made of the same material as the artificial blood vessel.

Reference numeral 5 indicates a connector. Connector 5 is formed of a member having a bioaffinity (biocompatibility) member having such as hydroxyapatite and other ceramics, polyester, PGA resin, CF resin, and other plastics, shape memory alloys, and metals such as titanium, and is hermetically sealed inside and has a vertically separable structure, with the upper part being 5a and the lower part being 5b. For example, when connector 5 is formed of a metal, a living body contact surface may be mirror-polished, and then subjected to a hydrothermal treatment by immersion in a supersaturated aqueous solution containing phosphoric acid and calcium, as described above.

It is preferable that, when upper part 5a and lower part 5b are separated from each other, connector 5 is in a state in which blood removal port 5b1 and blood return port 5b2 on lower part 5b side are closed, and when combined with upper part 5a, an opening and closing part for communication between upper part 5a and lower part 5b is formed. Further, it is preferable that the parts that is to be contacted with a living tissue in the other resins, plastics, metals, or ceramic materials used in the examples have at least biocompatibility (bioaffinity).

Reference numeral 6 indicates a blood circuit formed outside the patient's body. Blood circuit 6 forms a blood flow from blood removal port 5a1, blood drive pump 7, dialyzer 8, and blood return port 5a2. Blood circuit 6 is connected to a dialysis device commonly used for dialysis.

Reference numeral 7 indicates a blood drive pump. Blood drive pump 7 is exemplified by a drive pump for forming a blood flow of approximately 200 ml/min, for example, a rotating member with electrical input (it is preferable to be able to make an adjustment of the variation in the number of revolutions, etc., by adjusting the electrical input) such as a roller-type pump that forms a blood flow by rotating an impeller.

Reference numeral 8 indicates a dialyzer. Dialyzer 8 contains about 10,000 hollow fibers provided with holes on the side surfaces, and has a structure in which blood flows inside the hollow fibers and dialysate flows outside the hollow fibers in a direction opposite to the blood. Reference numeral 9 indicates a lid part. Lid part 9 has a shape that can be inserted and mounted on connector lower part 5b in a sealed state, and may be provided with a sealing to form a hermetic seal. Lid part 9 may be a multiple lid, such as a double lid, in which each lid may be provided with a sealing.

Reference numeral 10 indicates an on-off valve. On-off valve 10 is closed as it is when lid part 9 is mounted, but is opened when connector upper part 5a is mounted so that the upper and lower conduits communicate with each other. FIG. 4 shows an example of this configuration.

Reference numeral 11 indicates a flow channel for blood removal. Reference number 12 indicates a flow channel for blood return. Flow channel 12 for blood return is formed in connector 5 as a cavity or an extension of the tubular body. Reference number 13 indicates a blood removal side (arterial side) blood flow channel of blood circuit 6 in the blood removal side flow channel. Reference numeral 16 indicates a blood removal side (arterial side) blood flow channel of blood circuit 6 in the blood return side flow channel.

Reference numeral 15 indicates a dialysate supply flow channel. Dialysate supply flow channel 15 is for supplying a dialysate to dialyzer 8. Reference numeral 14 indicates a dialysate return flow channel. Dialysate return flow channel 14 is for supplying a dialysate containing excess water and wastes to an external discharge device (not shown).

Next, the operation will be described.

Percutaneous device 1 is implanted in the skin, and the arterial side end of internal shunt tubular body 2 is connected to artery 1B on the upper arm 1A, and the venous side end of internal shunt tubular body 2 is connected to vein 1C, in the same manner as when forming an internal shunt using an artificial blood vessel in hemodialysis treatment. The connection is made in the same way as when connecting an artificial blood vessel. The lower part of the connector (5b) already has blood removal tubular body 3 and blood return tubular body 4 fixedly attached thereto. One end of blood return tubular body 4 is connected to vein 1D. With this series of connections and arrangements in place, the patient should be left to rest with a protective cover (not shown) or the like until suturing and fixation.

After rest, lid part 9 is removed, and connector 5a shown in FIG. 1A is attached to form blood circuit 6, and then hemodialysis treatment is performed. FIG. 2 is a diagram for illustrating the operation at that time. The percutaneous device is half embedded in the skin (the lower part from 2a in FIGS. 1A to 1B and 2) and is hidden. For clarity of explanation, the whole is shown in solid lines.

The embodiments shown in FIGS. 1A-1B and FIG. 2 show a configuration in which a tubular body branched off from a part of an artificial blood vessel is used when an internal shunt is formed of the artificial blood vessel, thereby reducing the number of sutures with the blood vessel. However, even with a normal internal shunt formed, an embodiment of the present invention can be formed using the second blood removal tubular body 31 as shown in FIG. 3. The second blood removal tubular body 31 is formed of the same material as blood removal tubular body 3 shown in FIGS. 1A-1B. The percutaneous device is half embedded in the skin (the lower part, from 1A in FIG. 3) and is hidden, but for clarity of explanation, the whole is shown in solid lines.

Another embodiment of the present invention will be described with reference to FIGS. 4 to 6. Reference numeral 401 indicates a cover member. Cover member 401 is made of a plastic material such as Teflon®, PET, PP, or the like, and has a configuration for covering and fixing skin contact body 402 from above.

Reference numeral 401a indicates an outer peripheral edge, which is formed integrally with cover member 401 and extends to the outer periphery for stabilizing the percutaneous device.

Figure 4A:
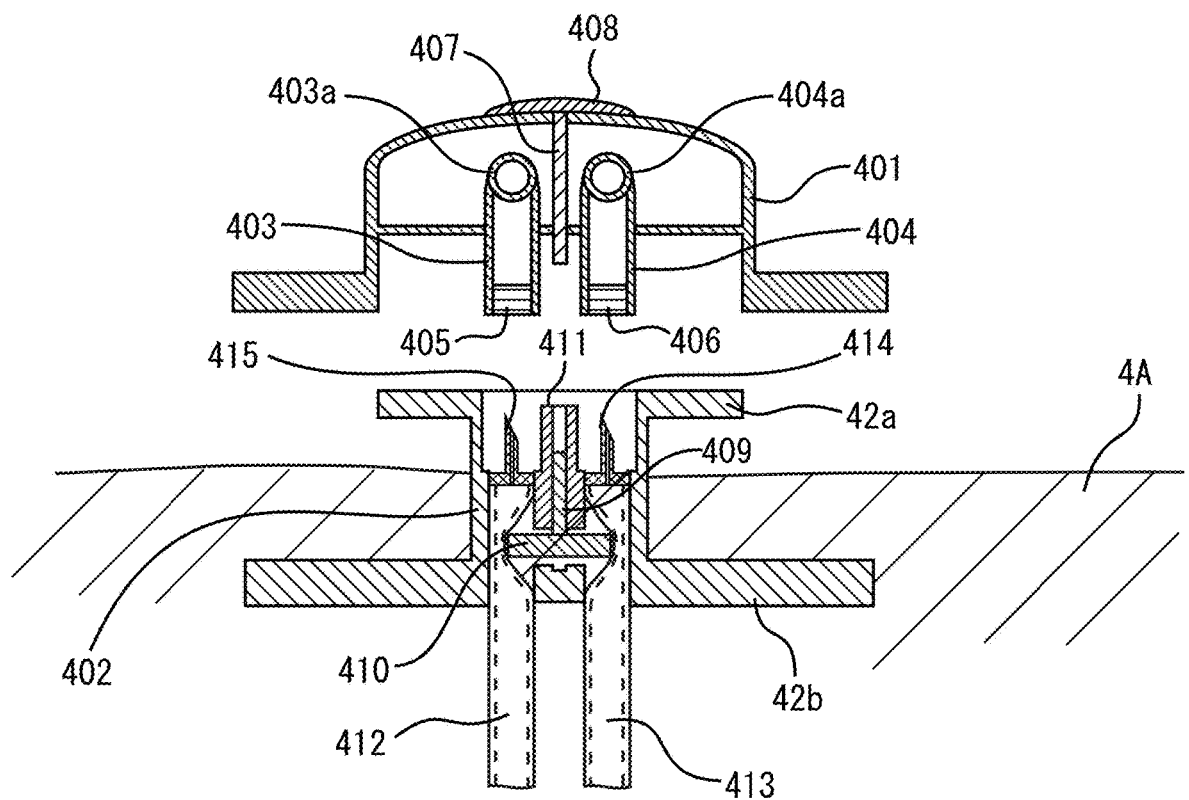
FIGS. 4A and 4B are diagrams showing another embodiment of the present invention.

Reference numeral 402 indicates a skin contact body, which is formed of the same material and in the same shape as the percutaneous device shown in FIGS. 1A and 1B. Reference numeral 403 indicates a connector for blood return, which is formed of a biocompatible rigid tubular body made of a plastic material, glass, metal, or the like, and one end is connected to blood return tube 403a, and a plug 405 for blood return made of a rubber or plastic material is fixed to the opening of the other end. Reference numeral 404 indicates a connector for blood removal, which is formed of the same rigid tubular body made of a plastic material, glass, metal, or the like, as described above, and one end is connected to blood removal tube 404a, and a plug 406 for blood removal made of a rubber or plastic material is fixed to the opening of the other end. In FIG. 4A, the top and bottom edges of the skin contact are indicated by reference numerals 42a and 42b, respectively.

Plug 405 for blood return and plug for blood removal 406 are made of the same material as the rubber plug of commonly used blood collection tube, and have a hardness that allows puncture hollow body 414 for blood removal and puncture hollow body 415 for blood return to penetrate therethrough. Reference numeral 407 indicates a transmitter A. Transmitter 407 is formed of a rod-shaped body of a hard plastic material or metal, one end of which is connected to an operation part 408, and the other end of which can be detachably joined to the transmitter for the opening/closing unit.

Operation part 408 is made of a plastic material, titanium material, etc., and is used to carry out an operation for closing tubular body 412 for blood returning part and tubular body 413 for blood removing part. Operation part 408 is a part to which a rotational force for rotating rotary valve 410 is applied. Reference numeral 409 indicates a transmitter for the rotary valve, which is formed of a rod-shaped body of a plastic material or metal and has a shape that allows rotary valve 410 to be connected to one end and the other end to be coupled to transmitter A. Transmitter 409 for the rotary valve is used to transmit the rotational force transmitted from the transmitter A to the rotary valve 410.

Figure 4B:
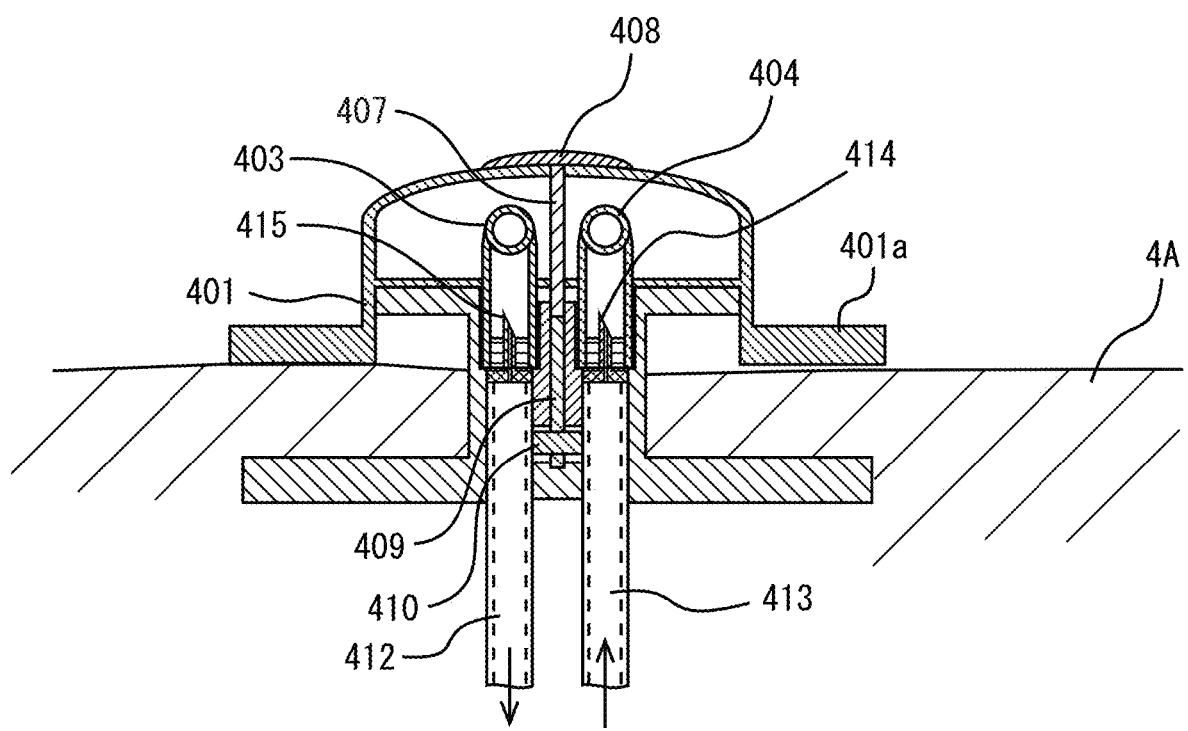

Reference numeral 410 indicates a rotary valve. Rotary valve 410 is rod-shaped, and has a size at least in the short axis direction equal to or larger than the diameter of the tubular body. It is rotatable from the state of closing the tubular body by local pressure from the side as shown in FIG. 4a to releasing the tubular body from local pressure as shown in FIG. 4b. Reference numeral 411 indicates a guide body for maintaining the trajectory in order to cause transmitter A407 and transmitter 409 for the rotary valve to only rotate, and to suppress the left and right displacement, and is made of a metallic material such as a titanium material or a ceramic material.

Guide body 411 is housed with skin contacting body 402 and secures the tubular body to the interior of skin contact body 402, and may be a part of a support which allows the tubular body to deform efficiently to form an internal shut-off state when the rotary valve 410 rotates.

Reference numeral 412 indicates a blood return tubular bodying part. One end of tubular body 412 for blood returning part is connected to puncture hollow body 415 for blood return, and the other end of tubular body 412 for blood returning part is connected to blood return tubular body 4 shown in FIG. 2. Tubular body 412 for blood returning part may be integrally formed with blood return tubular body 4 shown in FIG. 2, if it is formed of a resin tube (e.g., a material of the artificial blood vessel described above) that is flexible enough to be deformed and closed by the pressure from rotary valve 410.

Reference numeral 413 indicates a tubular body for blood removing part. One end of tubular body 413 for blood removing part is connected to puncture hollow body 414 for blood removing part, and the other end of tubular body 413 for blood removing part is connected to blood removal tubular body 3 shown in FIG. 2. Tubular body 413 for blood removing part may be integrally formed with blood return tubular body 4 shown in FIG. 2, if it is formed of a resin tube (e.g., a material of the artificial blood vessel described above) that is flexible enough to be deformed and closed by the pressure from rotary valve 410.

Both tubular body 413 for blood removing part and puncture hollow body 414 for blood removal are hermetically sealed inside skin contact body 402 which is to be contacted with the percutaneous skin, and block the infection path. Reference numeral 414 indicates a puncture hollow body for blood removal. The tip of puncture hollow body 414 for blood removal is at least acutely angled so that it can pierce through plug 406 for blood removal.

Reference numeral 415 indicates a puncture hollow body for blood return. The tip of puncture hollow body 415 for blood return is at least acutely angled so that it can pierce through plug 405 for blood return. Reference numeral 416 indicates a fixed band. Fixing band 416 is formed integrally with cover member 401, and holds the connector on the percutaneous device in a state where it is wrapped around the arm and fixed. There are various ways of fixing and holding, and for example, a tubular body in the form of a wrist watch belt or a tubular body made of an elastic or stretchable member, such as a rubber band, may be used therefor.

Figure 5:
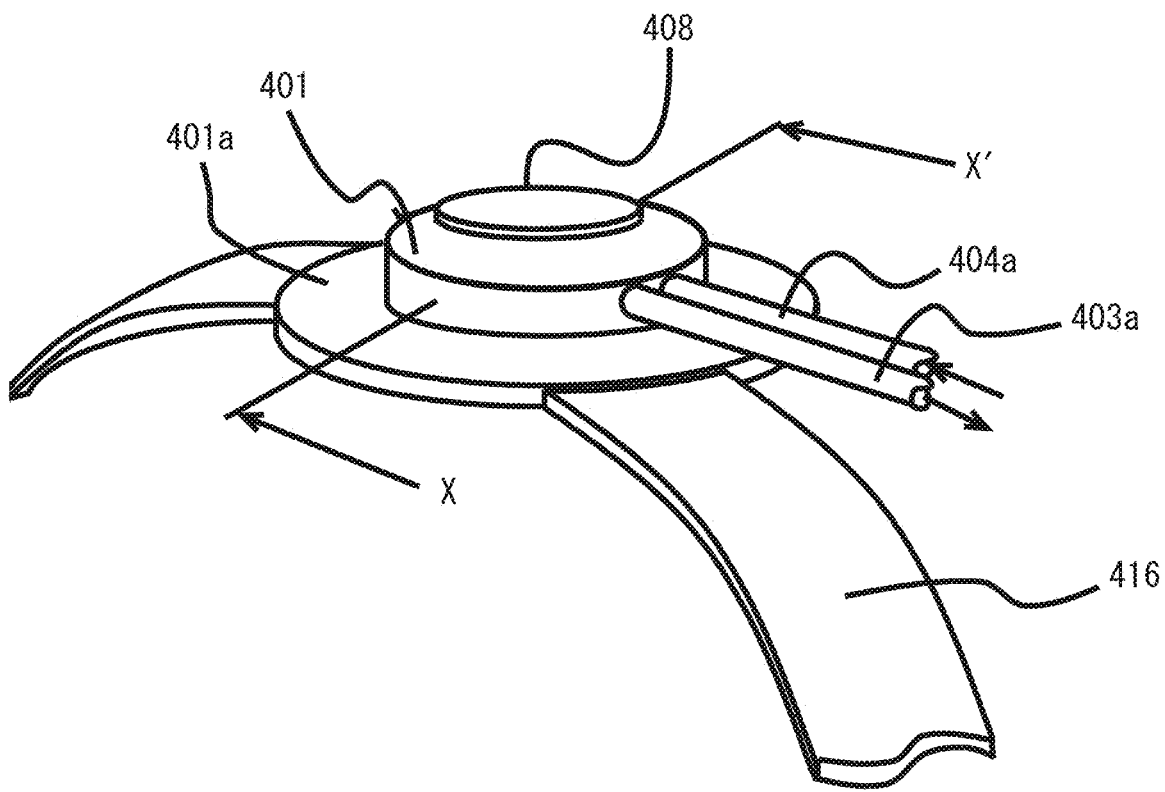
FIG. 5 is a diagram showing another embodiment of the present invention.

FIG. 5 shows a state in which lid part 417 is attached and a state in which the lid is removed in circumstances other than during dialysis treatment. Lid part 417 is used to shut off puncture hollow body 414 for blood removal and puncture hollow body 415 for blood return from outside to prevent infection at a time other than during dialysis treatment, and is used to prevent blood coagulation.

Lid part 417 can be formed of the same material as cover member 401. Cap 418 for blood removing part and cap 419 for blood returning part are provided on the bottom side of lid part 417 for holding puncture hollow body 414 for blood removal and puncture hollow body 415 in a punctured state. Lid part 417 is preferably used only for one-time use. Since the configuration other than the lid part is the same as that of the percutaneous device shown in FIG. 3, the same symbols are used and explanation thereon is omitted.

Cap 418 for blood removing part has a hollow cylindrical shape, and has a length enough to cover the entire puncture hollow body 414 for blood removal. Cap 418 for blood removing part can be formed of a material such as urethane or natural rubber. Inside cap 418 for blood removing part, there is provided a rod-shaped core 418a for blood removing part that is inserted into the hollow part of puncture hollow body 414 for blood removal so as to prevent blood from coagulating in puncture hollow body 414 for blood removal. The surrounding area is impregnated and coated with a blood coagulation inhibitor.

Cap 419 for blood returning part has a hollow cylindrical shape, and has a length enough to cover the entire puncture hollow body 415 for blood removal. Cap 419 for blood returning part can be formed of a material such as urethane or natural rubber. Inside cap 419 for blood returning part, there is provided a rod-shaped core 419a for blood returning part that is inserted into the hollow part of puncture hollow body 415 for blood return so as to prevent blood from coagulating in puncture hollow body 415 for blood return. The surrounding area is impregnated and coated with a blood coagulation inhibitor.

Figure 6A:
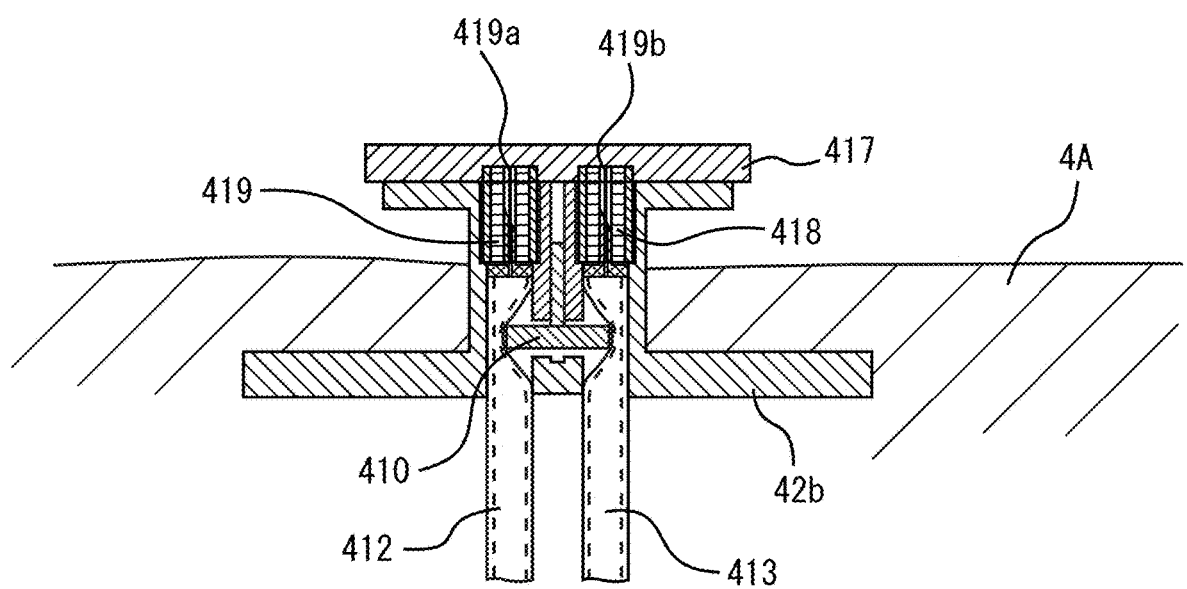
FIGS. 6A and 6B are diagrams showing another embodiment of the present invention.
Figure 6B:
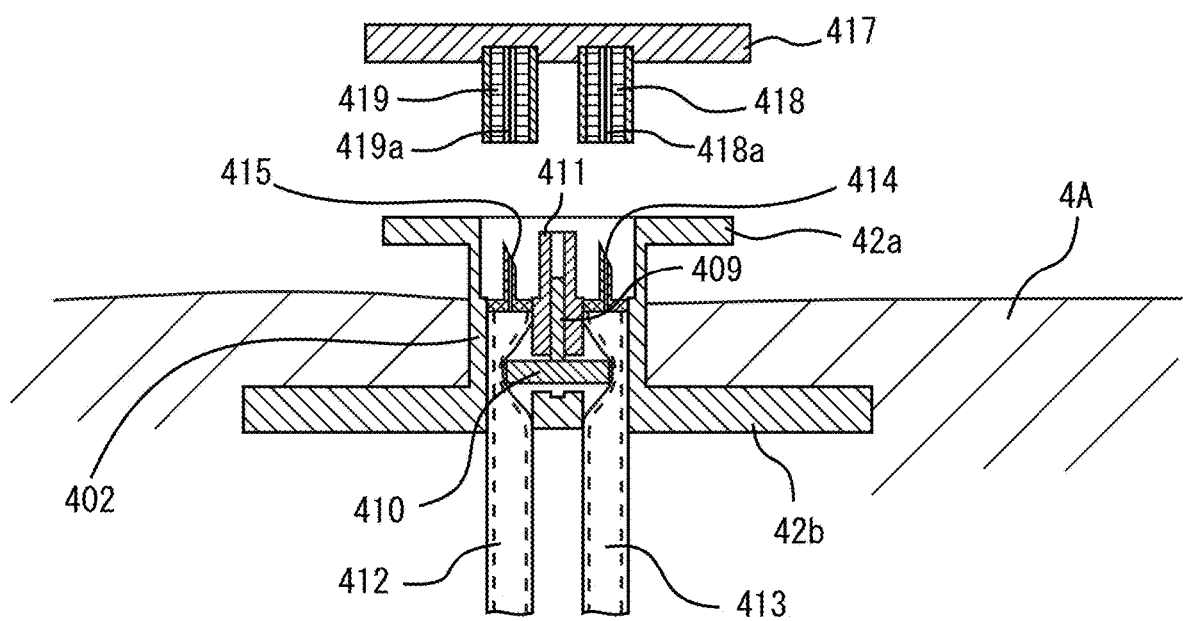

Next, the operation of the embodiment shown in FIGS. 4A to 4B, 5, and 6A to 6B will be described. As shown in FIGS. 1A and 1B and 3, implantation of skin contacting body 402 and formation of the internal shunt are performed on the skin. As shown in FIG. 6A, cap 418 for blood removing part and cap 419 for blood returning part of lid part 417 are punctured by puncture hollow body 414 for blood removal and puncture hollow body 415 for blood return, respectively, to protect puncture hollow body 414 for blood removal and puncture hollow body 415 for blood return and to shut off puncture hollow body 414 for blood removal and puncture hollow body 415 for blood return from the outside. Rotary valve 410 is configured to press tubular body 412 for blood returning part and tubular body 413 for blood removing part from the outside, respectively, for forming a blocked state and to prevent blood, etc., from leaking out of puncture hollow body 414 for blood removal and puncture hollow body 415 for blood return.

As described above, in addition to the blood coagulant being applied to each of cap 418 for blood removing part and cap 419 for blood returning part, the combination of core 418a for blood removing part and cap 418 for blood removing part acts as a plug for puncture hollow body 414 for blood removal and the combination of core 419a for blood returning part and cap 419 for blood returning part acts as a plug for puncture hollow body 415 for blood return, thereby preventing blood leakage.

At the time of use, lid part 417 is removed, and cover member 401 shown in FIGS. 4A and 4B is inserted and mounted. When puncture hollow body 414 for blood removal pierces through plug 406 for blood removal of cover member 401, tubular body 412 for blood returning part and connector 403 for blood return are connected to each other, and when puncture hollow 414 for blood removal pierces through plug 405 for blood return of cover member 401, tubular body 413 for blood removing part and connector 404 for blood removal are connected to each other. By these piercing, the connector is fixed on the percutaneous device, and it is preferable that the connector is further fixed by a fixing band 416.

When actuating part 408 is rotated, the rotation is transmitted to rotary valve 410 through transmitter A407 and transmitter 409 for rotary valve, and the rotary valve is rotated to reach the state shown in FIG. 4B, where blood flows into the blood circuit. After use, actuating part 408 is operated to rotate rotary valve 410 to return to the state shown in FIG. 4A, and tubular body 412 for blood returning part and tubular body 413 for blood removing part are blocked inside.

Rotary valve 410 should form a state in which the blockage of tubular body 412 for blood returning part and tubular body 413 for blood removing part is released as shown in FIG. 4B only during treatment, and cover member 401 is attached. A configuration in which the rotary valve rotates only when the cover member 401 is attached is preferable.

Rotary valve 410 is not necessarily required, and it should be able to be replaced without blood leaking from the puncture hollow body at least when replacing the lid and connector. For example, a sealed space covering the connector of the percutaneous device is formed to prevent blood from leaking out of the hollow body under high pressure, and then the exchange is performed.

The present invention should have a configuration which leads to no leakage of blood when blocking and connecting the blood flow directly connected to an artery, and this configuration should be simple and infection-free.

The present embodiment has a simple configuration, is easily connected to the blood circuit formed during hemodialysis with a simple configuration, and has a configuration that is free of infection and other burdens for the patient.

Next, another embodiment of the present invention will be described with reference to FIGS. 7A and 7B.

Figure 7A:
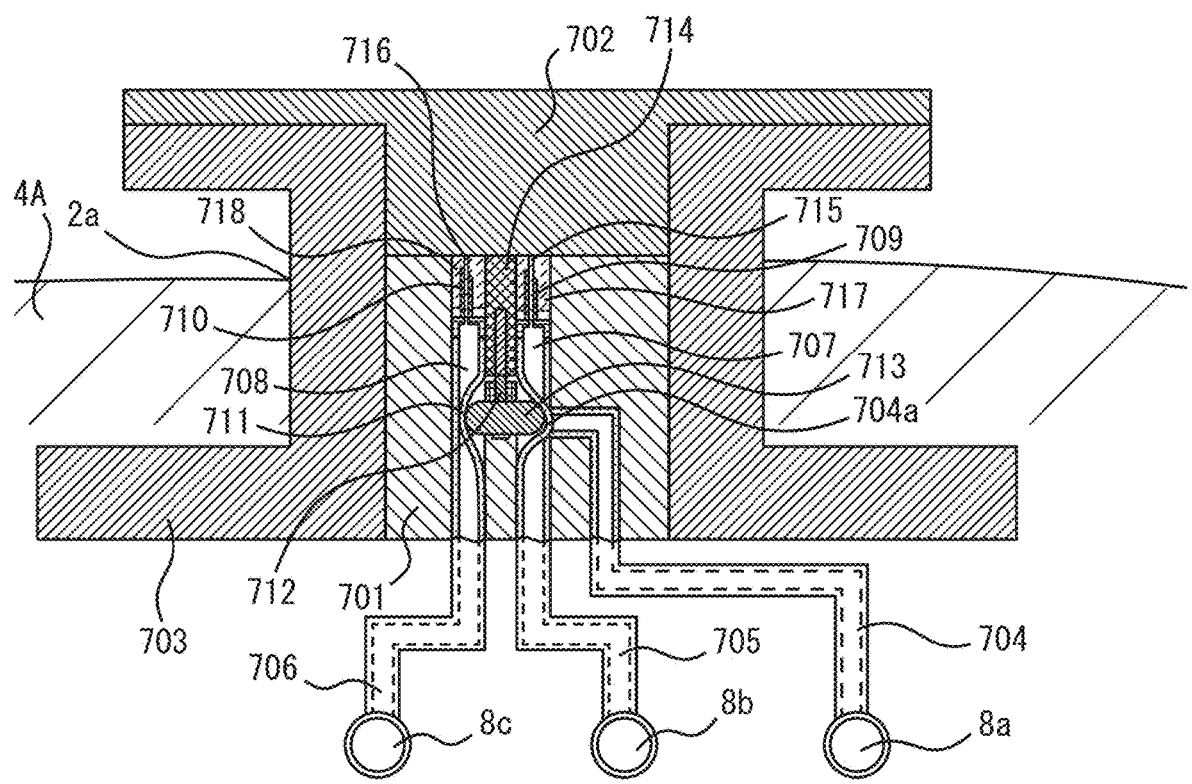
FIGS. 7A and 7B are diagrams showing another embodiment of the present invention.

In FIG. 7A, reference numeral 701 indicates the lower part of the connector. Connector lower part 71 may be formed of a resin, metal, ceramics, or the like. Inside connector lower part 71, a flow channel for blood removal and a flow channel for blood return are formed, and a fluid circuit configuration that opens and closes the flow channels by an external driving operation to adjust the flow amount. Since the bottom part of the connector lower part has a contact surface with a living tissue, this portion is covered with a biocompatible member, or connector lower part 701 itself is formed of a biocompatible member. Reference numeral 8a indicates an artery, and reference numerals 8b and 8c indicate veins.

Reference numeral 702 indicates a lid part. Lid part 702 is inserted and arranged so as to cover cap 717 for blood removal and cap 718 for blood return at a time other than during hemodialysis treatment, and fixing stopper 714 at the bottom part has a mating relationship with a convex portion 711 in order to fix convex portion 711 so as not to rotate. Reference numeral 703 indicates a skin contact body. Skin contact body 703 has a bobbin-shaped cylinder with the diameter of the bottom part larger than the diameter of the top part. Skin contact body 703 may be formed of a biocompatible member such as the hydroxyapatite dense body as described above. Skin contact body 703 is implanted in the skin when connecting the artificial blood vessel to an artery and veins so that the top part is exposed on the skin. Reference numeral 704 indicates an arterial side tubular body. Arterial side tubular body 704 may be formed of a material used for an artificial blood vessel or the like. Reference numeral 705 indicates venous side tubular body A. Veneous side tubular body 705 may be formed of a material used for an artificial blood vessel or the like. Arterial side tubular body 704 and venous side tubular body A705 are connected at the other end so that an internal shunt can be formed. FIGS. 7A and 7B.

Reference numeral 706 indicates a blood return tubular body. One end of blood return tubular body 706 is connected to vein 8c, and the other end is connected to puncture hollow body 710 for blood return via blood return tubular body A708. Reference numeral 707 indicates a blood removal tubular body. Blood removal tubular body 707 is connected to venous side tubular body A705 and arterial side tubular body 704. Blood removal tubular body 707 is formed integrally with arterial side tubular body 704 and venous side tubular body A705, and preferably has no joint, and is a portion described for explanation in the embodiment. Blood removal tubular body 707 is arranged in connector lower part 701 such that it can be deformed and blocked by being pressed by valve body 713.

Reference numeral 708 indicates a blood return tubular body. Blood return tubular body 708 for is formed integrally with blood return tubular body 706, and the other end is connected to puncture hollow body 710 for blood return. Blood return tubular body 708 is shown separately from blood return tubular body 706 because it indicates the part that can be deformed and blocked by being pressed by the valve body. Artificial blood vessels, etc., have flexibility, but it is preferably made of a material that is unlikely to be damaged even if the deformation by the pressing force of valve body 713 is repeated. Reference numeral 709 indicates a puncture hollow body for blood removal. Puncture hollow body 709 for blood removal is in the form of a puncture needle, and has a diameter large enough to allow sufficient blood movement during dialysis.

Reference numeral 710 indicates a puncture hollow body for blood return. Puncture hollow body 710 for blood return is in the form of a puncture needle, and has a diameter large enough to allow sufficient blood movement during dialysis. Reference numeral 711 indicates a convex portion. Convex portion 711 is connected to valve body 713 via supporting connection part 712. When convex portion 711 is fitted into a concave portion and a rotational force is applied to convex portion 711 from the outside, the valve body is rotated. Reference numeral 712 indicates a supporting connection part. Supporting connection part 712 connects convex portion 711 and valve body 713 with a rod-shaped shaft, rotates in the long axis direction, and transmits the rotation of convex portion 711 to valve body 713. Reference numeral 713 indicates a valve body. Valve body 713 is rod-shaped. For example, Valve body 713 can be rotated 90 degrees around the axis of supporting connection part 712 to pressurize and block the tubular body, and can be rotated another 90 degrees to release the pressurized closure.

Reference numeral 714 indicates a fixing stopper. As described above, fixing stopper 714 has a concave portion for mating with the convex portion 711 as described above, and when the fixed stopper 714 mates with the convex portion 711, the valve body is fixed so that it does not rotate. Reference numeral 715 indicates a rod-shaped plug A. Rod-shaped plug 715 is inserted into the hollow part of puncture hollow body 709 for blood removal to prevent hollow body 709 from being clogged with a thrombus or the like. Reference numeral 716 indicates a rod-shaped plug B. Rod-shaped plug 716 is inserted into the hollow part of blood return puncture hollow body 710 to prevent hollow body 710 from being clogged with a thrombus or the like. Reference numeral 717 indicates a cap for blood removal. Cap 717 for blood removal covers the periphery of puncture hollow body 709 for blood removal to protect and fix it. Reference numeral 718 indicates a cap for blood return. Cap 718 for blood return covers the periphery of puncture hollow body 710 for blood return to protect and fix it. Cap 717 for blood removal and cap 718 for blood return are made of an elastic material formed of natural rubber, resin, or the like, that can be penetrated through by puncturing with the hollow body.

Figure 7B:
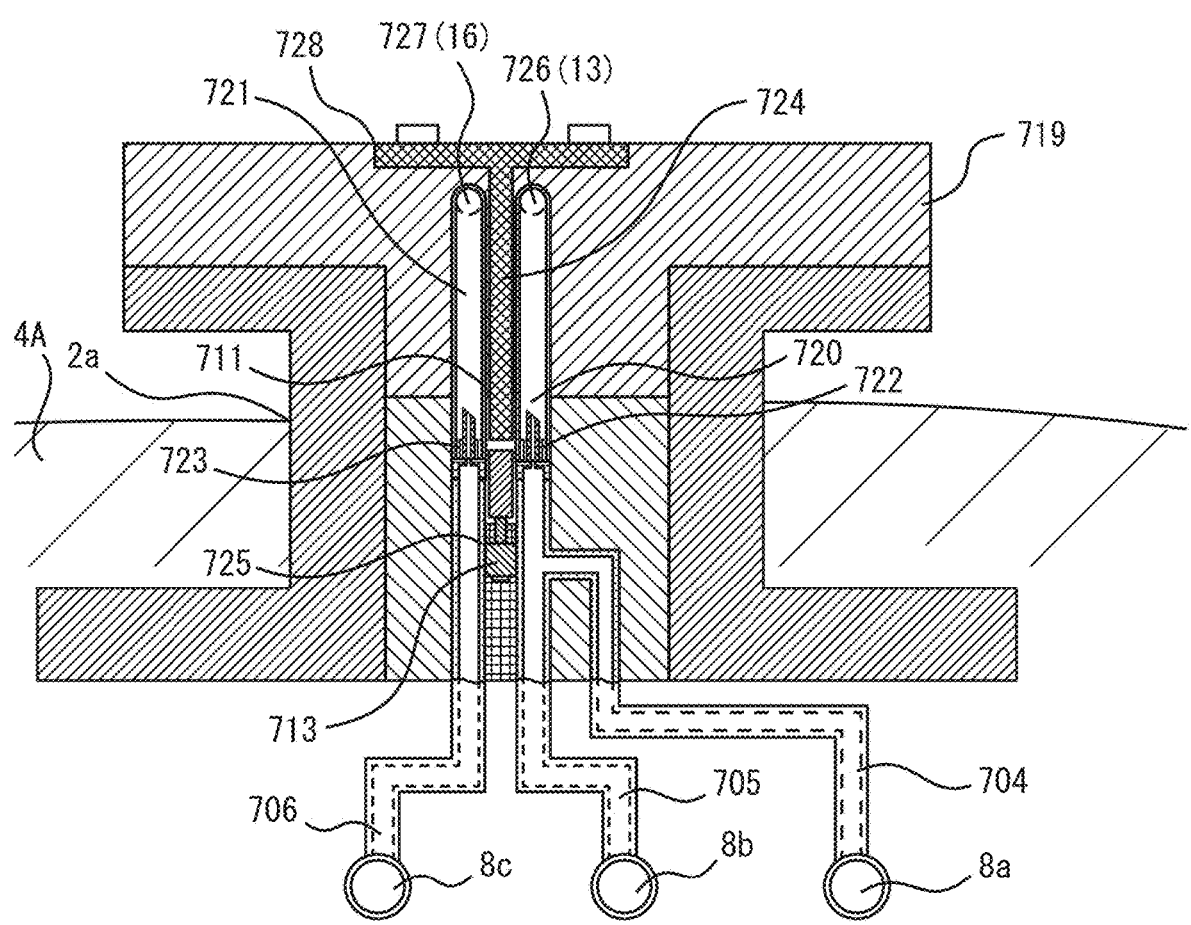

In FIG. 7B, reference numeral 719 indicates the upper part of the connector. Connector upper part 719 incorporates blood removal tubular body 720 for supplying blood to blood circuit 6 outside the living body and blood return tubular body 721 for returning blood returned via blood circuit 6 to the body. Connector upper part 719 also has rotary actuating part 728 for rotating the valve body formed in the upper center. Reference numeral 720 indicates a blood removal tubular body. One end of blood removal tubular body 720 is connected to blood removal side tubular body 726 for blood circuit, and the other end is connected to stopper A722. Reference numeral 721 indicates a blood return tubular body. One end of blood return tubular body 721 is connected to blood return side tubular body 727 for blood circuit of the blood circuit, and the other end is connected to stopper B723. Reference numeral 722 indicates plug A. Plug 722 may be made of a rubber or resin that can be pierced and penetrated through by the hollow body for blood removal. After penetration, plug 722 has a structure that prevents blood leakage by exerting a force that presses the hollow body.

Reference numeral 723 indicates plug B. Plug 723 may be formed of a rubber or resin that can be pierced and penetrated through by the hollow body for blood removal. After penetration, plug 723 has a structure that prevents blood leakage by exerting a force that presses the hollow body. Reference numeral 724 indicates a drive transmission shaft. Drive transmission shaft 724 is connected to concave portion 725 for driving, and transmits the rotation of rotary actuating part 728 to the valve body by mating concave portion 725 for driving with convex portion 711. Reference numeral 725 indicates a concave portion for driving. Concave portion 725 for driving has a shape that mates with convex portion 711, and is used to rotate convex portion 711 and rotate valve body 713 while mated with the convex portion 711, and is preferably formed of a non-deformable and durable resin or metal. Reference numeral 726 indicates a blood removal side tubular body for blood circuit. Blood removal side tubular body 726 for blood circuit corresponds to blood removal side (arterial side) blood flow channel 13 shown in FIG. 1, and reference numeral 727 indicates a blood return side tubular body for blood circuit and corresponds to blood removal side (arterial side) blood flow channel 16 shown in FIG. 1. Specifically, blood removal side tubular body 726 for blood circuit and blood return side tubular body 727 for blood circuit have the same structure as the tubular body extending perpendicular to the long axis direction of the connector, as shown in FIG. 6. Reference numeral 728 indicates a rotary actuating part. Rotary actuating part 728 is rotatably placed parallel to the top of the connector upper part, and can be rotated with a fingertip. By this rotation, the valve body rotates and starts and stops blood circulation in the blood circuit.

Next, the operation of the embodiment shown in FIGS. 7A and 7B will be described. Before the treatment, lid part 702 is mounted on connector lower part 701, as shown in FIG. 7A. Skin contact body 703 is subcutaneously implanted into skin tissue 4A up to portion 2a. With lid part 702 attached, a plug body is inserted into puncture hollow body 709 for blood removal and puncture hollow body 710 for blood return, respectively, and valve body 713 is fixed so as not to rotate. Valve body 713 presses the tubular body to block it, while blocking an arterial bifurcation, so that the arterial flow is blocked from flowing in the vein direction. This blockage suppresses the effect on the veins and may help to avoid some of the shunt complications. During treatment, lid part 702 is removed. At this time, valve body 713 compresses and blocks the junction of the arterial side tubular body 704 and venous side tubular body 708, as well as the blood return tubular body. It is preferable that the blocked state is maintained during all periods other than the attachment of connector upper part 719, and a state detection sensor to monitor the blocked state and a computer chip may be built into the connector to form a system that can be monitored by an external computer via WiFi or infrared communication.

During treatment, lid part 702 is removed from the connector. Since plug body A715 and plug body B716 are inserted into puncture hollow body 709 for blood removal and puncture hollow body 710 blood return, respectively, they are removed. When the plug bodies are removed, the mating state of fixing stopper 714 with convex portion 711 is also released, but the state of convex part 711 does not change and remains rotated in the direction of fixing valve body 713, so that blood does not leak out. Next, connector upper part 719 is attached in place of lid part702, and at the same time, puncture hollow body 709 for blood removal and puncture hollow body 710 for blood return pierce through plug body A722 and plug body B723, respectively. The tip of drive transmission shaft 724 mates with convex portion 711. When the rotary actuating part 728 is turned, drive transmission shaft 724 rotates, and convex portion 711 and concave portion 725 for driving rotate as well. This rotation causes the arterial flow to flow to blood removal tubular body 720 and venous side tubular body A705, forming a blood flow at a predetermined speed in blood circuit 6 shown in FIG. 1.

Although valve body 713 block joint 704a between arterial side tubular body 704 and venous side tubular body A705 in the state shown in FIG. 7A, the blocked state is gradually released by the rotation of concave portion 725 or driving. The amount of rotation of valve body 713 allows the adjustment of the amount of blood supply from the artery, and in fact, a shunt is formed only during dialysis treatment, so that some of shunt complications may be improved.

Figure 8A:
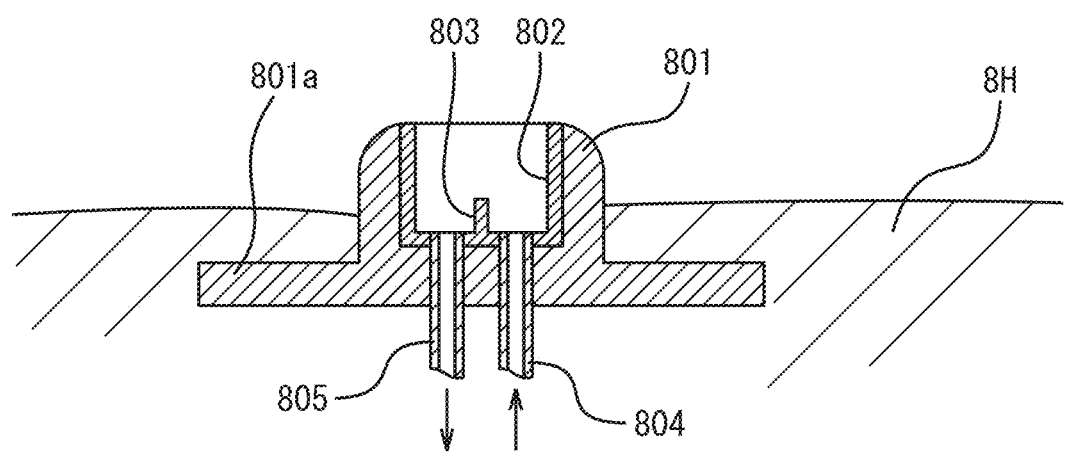
FIGS. 8A to 8D are diagrams showing another embodiment of the present invention.
Figure 8B:
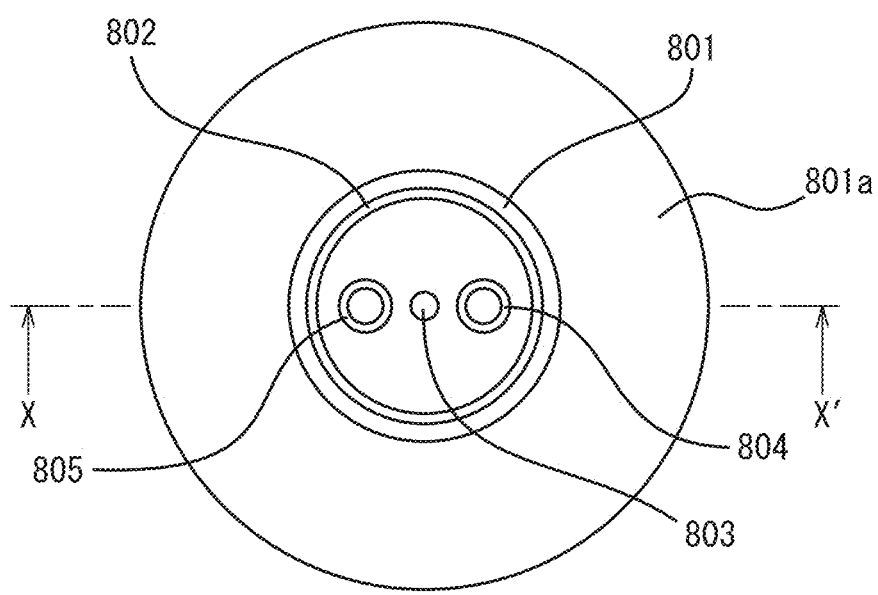
Figure 8C:
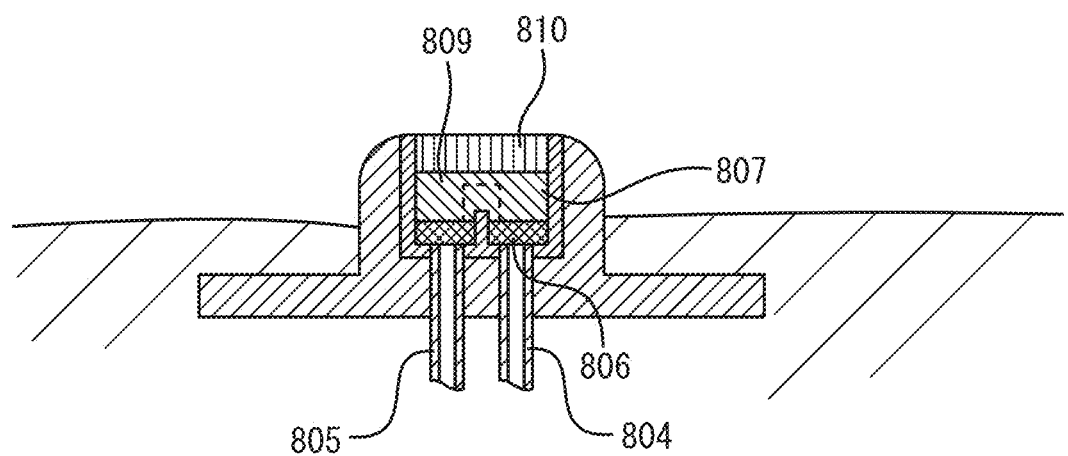
Figure 8D:
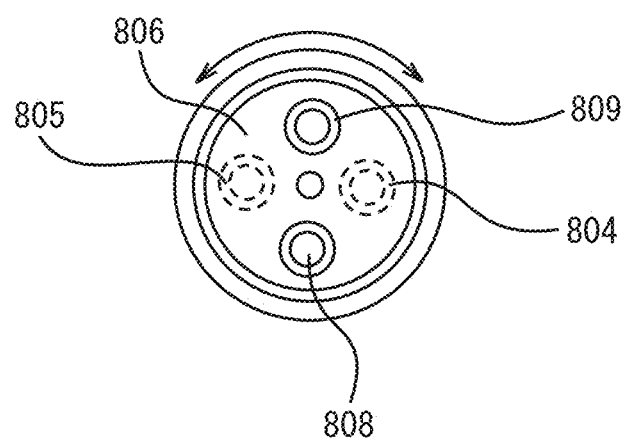

Other embodiments will be described in detail with reference to FIGS. 8A to 8D. In FIGS. 8A and 8B, reference numeral 801 indicates a terminal part. FIG. 8A shows a cross section of terminal part 801 taken along a plane including the axis of terminal part 801. FIG. 8A shows terminal part 801 partially embedded in the patient's skin 8H. FIG. 8B is a plan view of terminal part 801 as viewed from the top. Reference numeral 801a indicates the bottom edge of terminal part 801. As shown in FIG. 8A, the top peripheral edge of the upper portion of terminal part 801 is chamfered and rounded, and a concave portion is formed in the center of the upper portion of terminal part 801. As shown in FIG. 8B, terminal part 801 has a circular shape in a plane perpendicular to the axis. Guide body 802 having an upward opening is formed in a shape along the concave portion. Reference numeral 802 indicates a guide body. Guide body 802 may be made of a metal such as titanium, ceramics such as alumina, zirconia, or carbon, or a resin such as Teflon or polyethylene, and is a member having at least biocompatibility. It is preferable that guide body 802 has a strength against cutting and impact resistance. Reference numeral 803 indicates a shaft portion. Since shaft portion 803 is formed integrally with guide body 802, and the rotary valve rotates about 90 degrees around shaft portion 803, it is necessary for shaft portion 803 to have a durable strength that does not cause breakage easily. When rotary valve 806 can rotate at a predetermined angle without requiring shaft portion 803, shaft portion 803 may not be required.

Reference numeral 804 indicates a blood removal tubular body. Blood removal tubular body 804 is made of an artificial blood vessel used for a shunt for hemodialysis. Reference numeral 805 indicates a blood return tubular body, which is made of an artificial blood vessel used for a shunt for hemodialysis. Reference numeral 806 indicates a rotary valve. Rotary valve 806 has a disk shape or a cylindrical shape, and may be made of a durable and biocompatible plastic material, resin, or ceramic. Rotary valve 806 can rotate around shaft portion 803. A member having antithrombotic properties is disposed on a surface of rotary valve 806 that comes into contact with blood removal tubular body 804 and blood return tubular body 805 by a method such as coating and lamination. In addition, The rotary valve is equipped with a bearing portion for shaft portion 803 at the center, or it may be rotated by contacting the wall of guide body 802, which is in contact with the circumference, without using shaft portion 803. Further, the rotary valve may be provided with a bearing portion for shaft portion 803 at the center, or it may be rotated by contacting the circumferential wall of guide body 802 without using the shaft 803.

Reference numeral 807 indicates a protective cover. Protective cover 807 is formed of a biocompatible metal, resin, or ceramic, is durable in the vertical direction, and is used to prevent the rotary valve from rotating in cases other than treatment, and to protect blood removal side connecting tubular convex portion 808 and blood return side connecting tubular convex portion 809 from forces from above. Blood removal side connecting tubular convex portion 808 is hollow and is formed integrally with rotary valve 806. Blood return side connecting tubular convex portion 809 is connected to a conduit extending from the dialysis apparatus. Reference numeral 810 indicates an integrated lid part. Integrated lid part 810 is formed after the dialysis treatment, and is formed of a layered structure of a ceramic material and a resin, or a prosthetic structure.

The layered structure means that a ceramic material and a resin powder are discharged and laminated by a so-called 3D printer, while, for example, adhesives are discharged and cured sequentially to form a laminated body, or calcium phosphate powder is spread and laminated while water, citric acid, or other organic acids are discharged and cured, or a photocurable resin powder is applied and laid down while being irradiated with ultraviolet light or other curing rays. The layered structure may also be obtained by spreading a ceramic powder and sequentially sintering it by laser light irradiation.

The prosthetic structure may be obtained by forming a resin-based prosthesis used in the oral cavity and then forming an integrated lid part 810, or by obtaining an article having the shape of the integrated lid part by CAM processing whereby grinding and cutting are performed on the basis of a computer program for a free-cutting ceramic (machinable ceramic) bulk material, and fixing it with an adhesive. It is preferable to form a lid part that is almost an integral part and cannot be removed manually. In other words, the integrated lid part is firmly joined so that it cannot be removed manually, and exhibits a state in which it looks at first glance as an integrated type. Integrated lid part 810 cannot be removed by itself, but is removed by cutting, melting, or other processing processes. Since it is attached by layered hardening, there is no infection from the percutaneous device and no special protection is required even in daily life, and it does not require special protection and can be handled without burden.

Next, the operation of the configuration shown in FIG. 8 will be described with reference to FIGS. 9 and 10. Reference numeral 901 indicates a processing tool. Processing tool 901 is used to remove integrated lid part 810 by cutting, grinding, melting, evaporating, or other means. Examples of the cutting, grinding, melting, evaporating, or other means for integrated lid portion 810 include milling, drilling, laser light, etc., for example, removal processing by CAM (Computer Aided Machine) with reduced vibration, melting by laser light, evaporation removal, rotary processing tools for resin, dental drills, end mills, etc. In the case of, for example, ceramics, integrated lid part 810 may have a low hardness and may be removed in a form that suppresses processing vibration. In the case of a resin cover, since it is easy to cut, and therefore, a material that is compatible with a living body and is easy to cut and process is preferable.

Integrated lid part 810 should be able to withstand at least a certain level of external stimulus and form a sealed state, and does not necessarily require biocompatibility. It may be bonded with an adhesive or the like, and forms a state that cannot be easily removed. The tight coupling to guide body 802 can prevent bacterial infection, etc.

After removing integral cover 810 with processing tool 901, protective cover 807 is removed. Reference numeral 807 indicates a protective cover for preventing bacterial infection and for removing external pressure on rotary valve 806, and has a function of a protective cover to protect against intrusion of residue when integrated lid part 810 is removed and against vibration during processing of integrated lid part 810. Protective cover 807 is formed of a resin or metal, or is formed of a non-deformable sterile material.

After removing protective cover 807, connector 903 for blood removal and connector 904 for blood return of access connector 902 extending from the dialysis apparatus are connected to blood removal side connecting tubular convex portion 808 and integrated lid part 810, respectively. Access connector 902 is a housing made of a plastic material or metal, has a robot arm structure, and extends from the dialysis apparatus. The connection between the access connector and the dialysis apparatus is preferably of a flexible cord type so that the patient can relax during the dialysis time, but may be in the form of a robot arm for a short time.

Figure 9A:
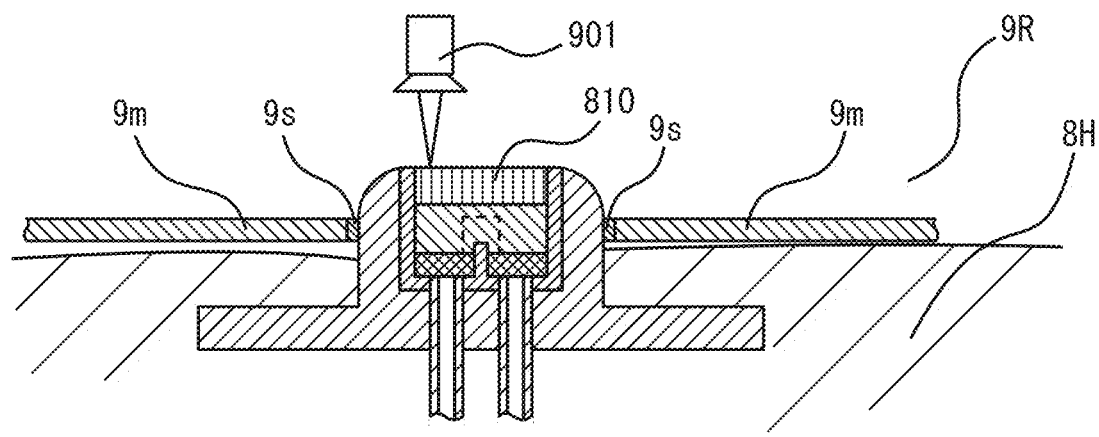
FIGS. 9A to 9D are diagrams showing the operation of another embodiment of the present invention.
Figure 9B:
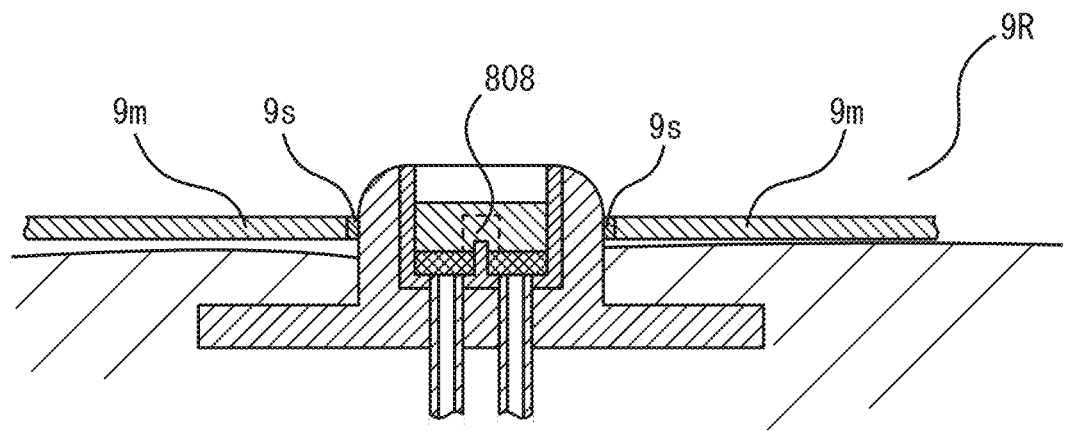
Figure 9C:
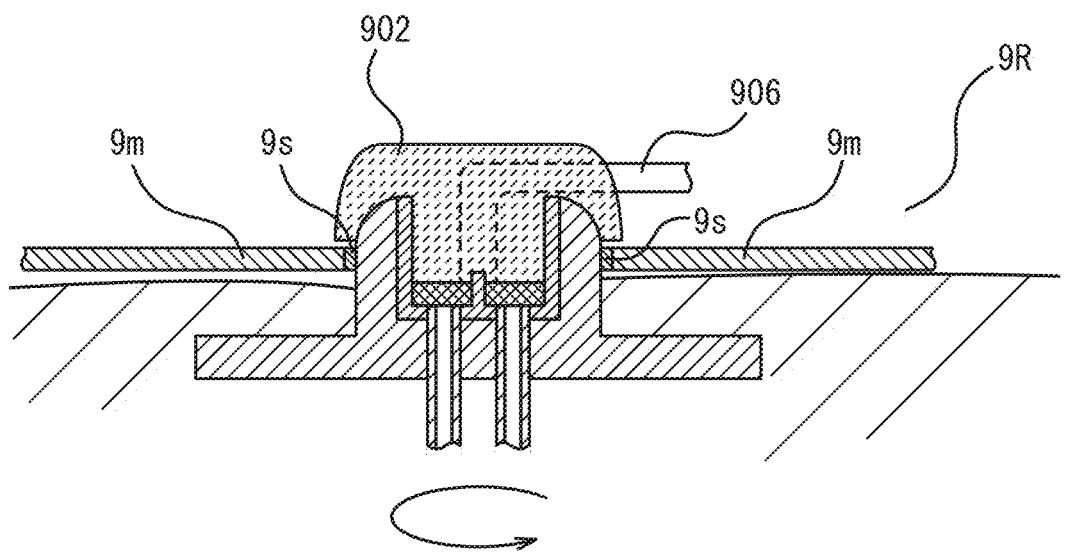

By rotating access connector 902, rotary valve 806 to which access connector 902 is attached is rotated by about 90 degrees. By this rotation, blood removal tubular body 804 and blood return tubular body 805 communicate with connector 903 for blood removal and connector 904 for blood return, respectively, thereby forming a blood circuit. When the dialysis treatment is completed, the access connector is rotated from the state of FIG. 10A to rotate the rotary valve. By the rotation of rotary valve 806, the opening of blood removal tubular body 804 and the opening of blood return tubular body 805 are shielded and fixed by the bottom surface of rotary valve 806, and then the access connector is removed. After the access connector is removed, protective cover 807 is attached (FIG. 9C). Further, while discharging a ceramic powder and the metal powder from the injection jig via nozzle 1001 and spreading it, laser light is irradiated to form a laminate. Alternatively, curing light such as ultraviolet light is irradiated while the photocurable resin powder is discharged from nozzle 1001 and spread, thereby forming integrated lid part 810.

The above steps are preferably performed automatically by CAM that includes one programmed computer process.

The working section by the CAM seals and holds the periphery of terminal part 801 implanted on the patient, and forms a sterilized working space on top. Terminal part 801 is sterilized by irradiation with ultraviolet radiation or application of a disinfectant while it is fixed in the work space. In this regard, FIG. 9A shows a hole-shaped upper holding portion 9s for holding terminal part 801 formed on working section bottom portion 9m. Working section 9R is omitted except for the working section bottom portion 9m.

As shown in FIG. 9A, integrated lid part 810 is cut and removed by a cutting tool using a laser beam, which is installed on a uniaxial or parallel link type manipulator. Next, as shown in FIG. 9B, protective cover 807 is removed using the manipulator. Access connector 902 is connected using the manipulator under a condition in which access connector 902 is positioned so that connector 903 for blood removal and connector 904 for blood return of rotary valve 806 are respectively connected to blood removal side connecting tubular convex portion 808, 809.

Figure 9D:
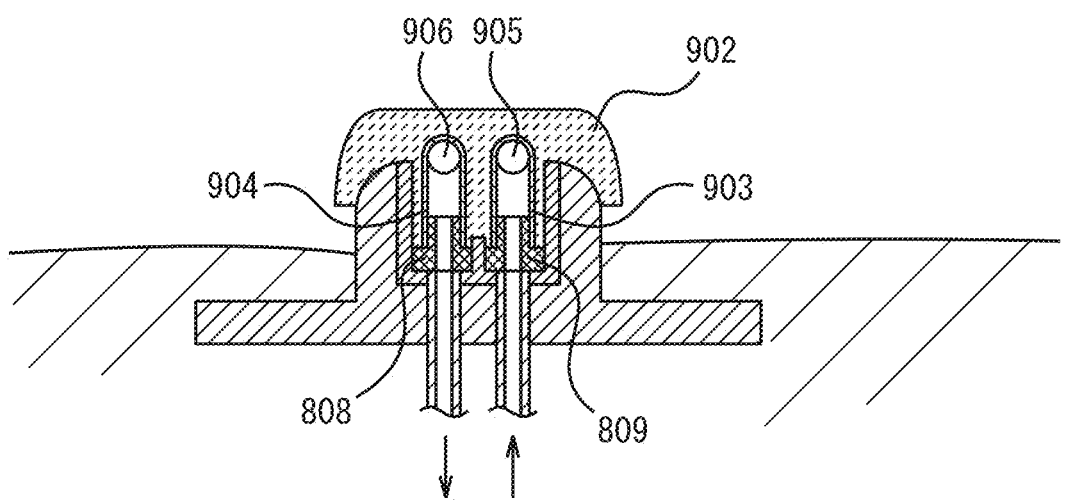

As shown in FIGS. 9C and 9D, access connector 902 is rotated to match or partially match blood removal side connecting tubular convex portion 808, 809 with blood removal tubular body 804 and blood return tubular body 805, thereby forming a blood circuit so that blood can be supplied to the dialysis apparatus. Reference numeral 905 indicates a conduit blood removal. Conduit 905 for blood removal is connected to connector 903 for blood removal and is a tubular body for sending blood in the body to the dialysis apparatus. Reference numeral 906 indicates a conduit for blood return. Conduit 906 for blood return is connected to connector 904 for blood return and is a tubular body for returning purified blood from the dialysis apparatus to the body. During the dialysis treatment, the terminal part can be removed from this working space, and conduit 905 for blood removal and conduit 906 for blood return extending from the dialysis apparatus can be extendable depending on the condition of the patient. Thus, the patient is relaxed and the dialysis treatment is established via access connector 902.

Figure 10A:
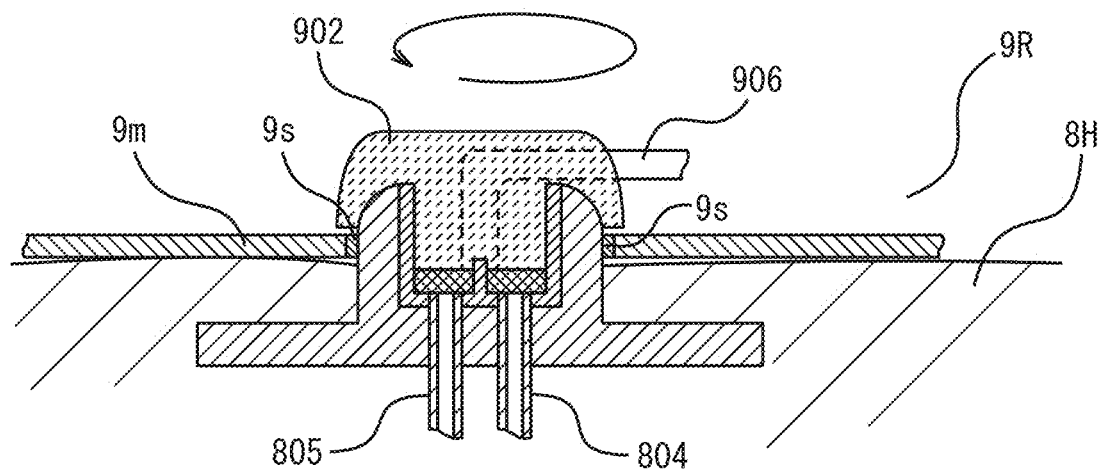
FIGS. 10A to 10D are diagrams showing the operation of another embodiment of the present invention.
Figure 10B:
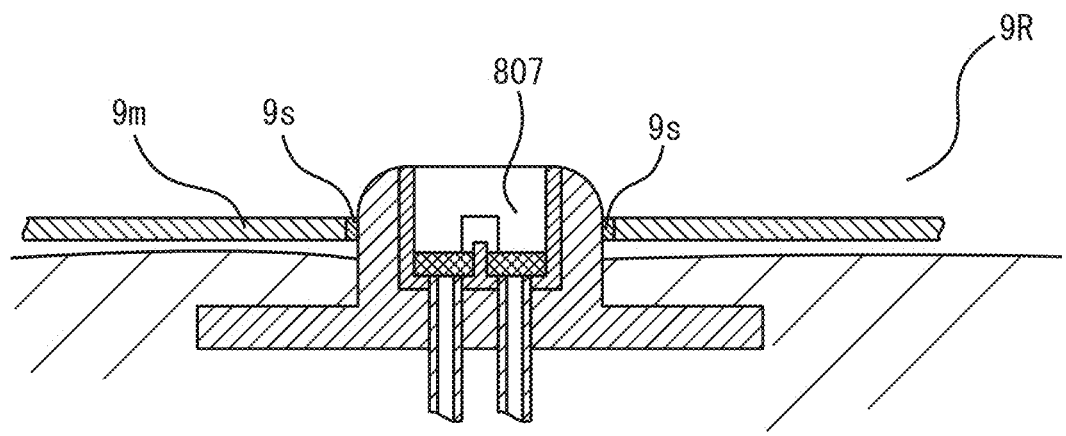
Figure 10C:
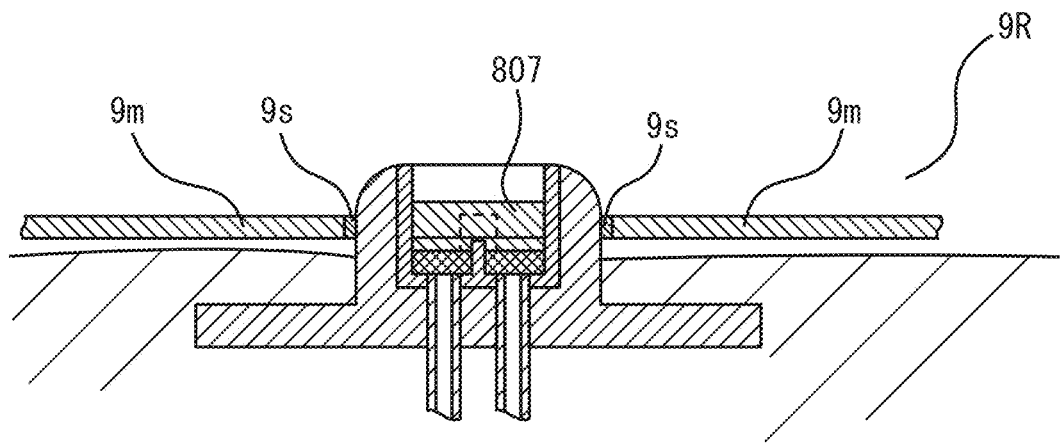
Figure 10D:
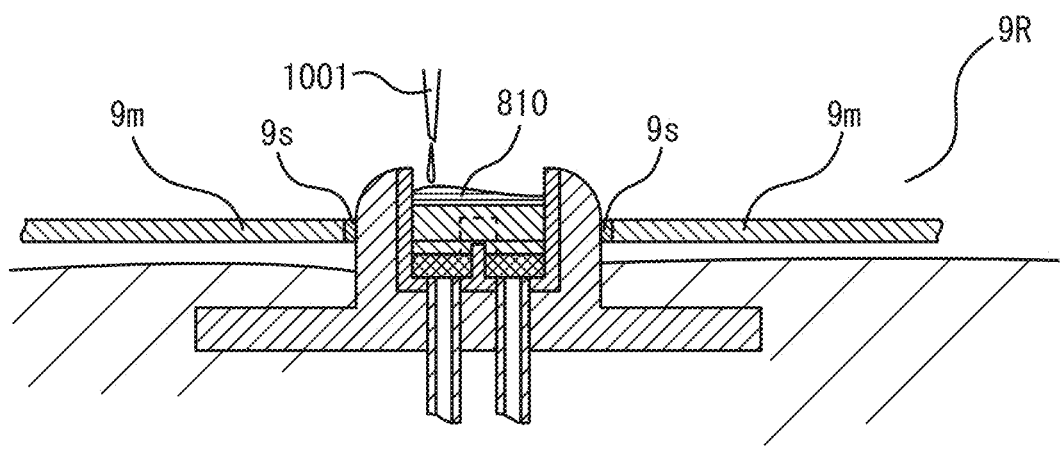

After the treatment, as shown in FIG. 10A, the upper part of terminal part 801 is again brought into contact with the terminal part holding hole of the working section. That is, the upper portion of the sealed terminal shown in FIG. 9A is cut by a laser beam or an electric mill. By these automated processes, hemodialysis can be performed at home or with only a drop-in at a medical institution.

Figure 11:
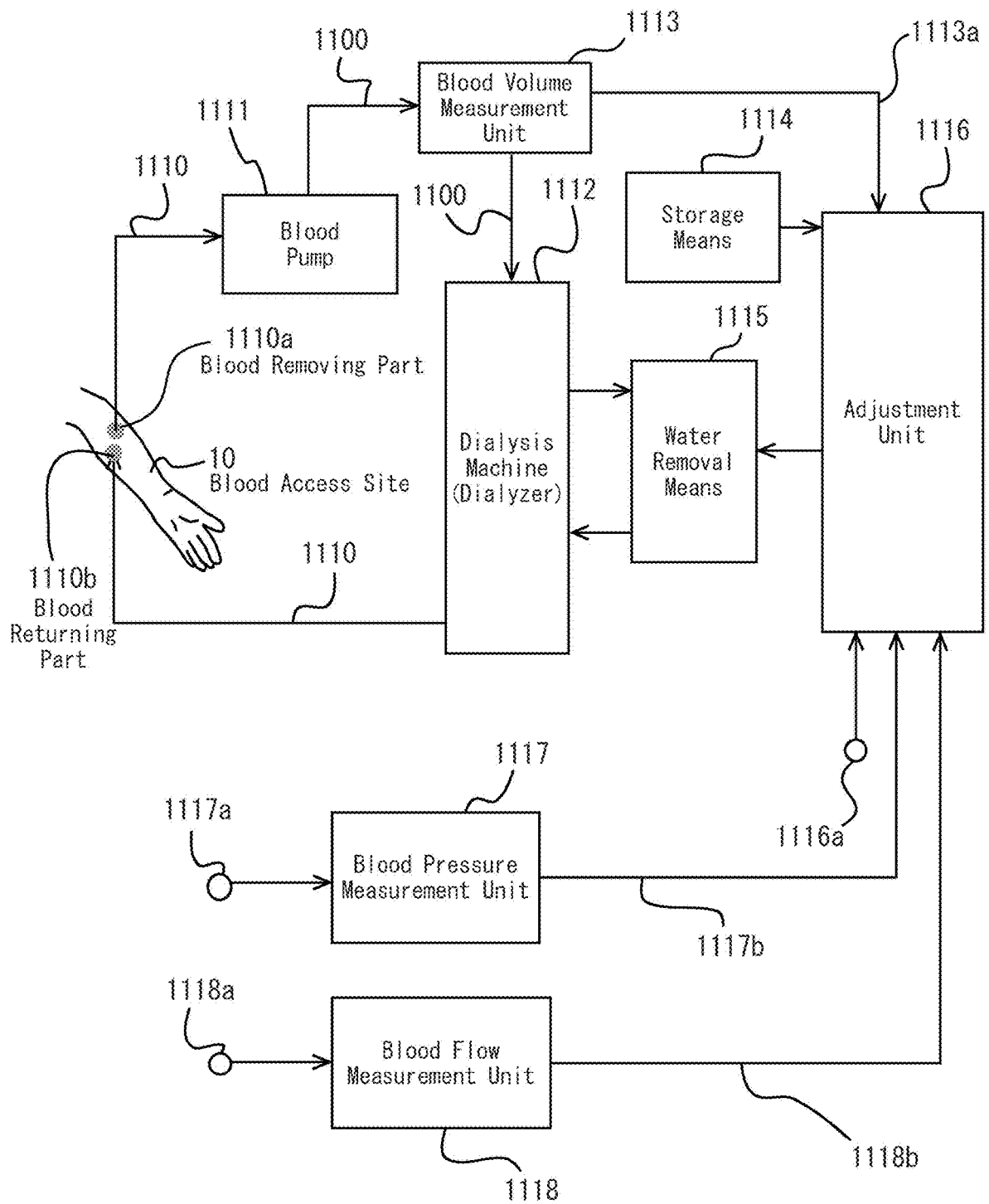
FIG. 11 is a diagram showing another embodiment of the present invention.

FIG. 11 shows an embodiment of the hemodialysis apparatus of the present invention, which will be described. This embodiment also effectively works for treatment by ordinary puncture except when a percutaneous device is used at a blood access site. In FIG. 11, reference numeral 1111 indicates a blood pump. Blood pump 1111 is used when blood is extracted from blood removing part 1110a to the outside. Blood pump 1111 can generate a blood flow of 200 ml per minute as a standard value, for example, in order to secure a sufficient blood flow in blood circuit 1100 generally formed outside the body. As blood pump 1111, for example, a roller-type pump may be used. When a roller-type pump is used as blood pump 1111, the roller-type pump may include an adjustment means comprising an electric control circuit that adjusts the rotation speed of an impeller forming the roller unit. The adjustment means supplies the adjusted electrical output to the blood flow driving pump by optimization signal output 1102a from individual difference information managing means 1102, and is adjusted so that the rotation speed becomes an optimum state. The blood circuit means a path through which blood taken from a patient flows during dialysis treatment.

Reference numeral 1112 indicates a dialysis machine composed of a dialyzer having inside a bundle of about 10,000 hollow fibers each having pores on the lateral surface, in which blood circulates inside the hollow fibers and a dialysate circulates outside the hollow fibers in the direction opposite to the flow of blood. Reference numeral 1113 indicates a blood volume measurement unit comprising a blood volume meter, a laser blood flowmeter, etc. For example, a laser beam is irradiated from the outer surface of a conduit constituting a blood circuit, and the reflected light from internal red blood cells, etc., is received by a sensor outside the conduit, and after deriving the blood volume from the sensor, the PRR value, etc., are calculated and output to adjustment unit 1116 as an electrical signal.

Reference numeral 1114 indicates a storage means. Storage means 1114 is comprised of a computer-readable storage medium such as a hard disk, a USB memory, a DVD, etc., and stores a water removal rate pattern, individual difference information of a patient, water removal adjustment data, etc. It also includes data from treatment at a dialysis treatment institution.

Reference numeral 1115 indicates a water removal means (water removing device). Water removal means (water removal device) 1115 is comprised of a dialysate circulation drive section, a water removal drive section, a waste storage section, etc., and supplies the dialysate to dialysis machine 1112, conveys excess body fluid and wastes such as uremic toxins, etc., mixed upon passing through the lateral surface of the hollow fibers of dialyzer 1112, releases the wastes to the outside by a filter, etc., and discharge the body fluid to be removed at a predetermined rate to the outside by an external drive unit or manual operation. Water removal means 1115 may be incorporated in a common hemodialysis apparatus, but a separate drive unit may be provided to automatically control the outlet for discharging the body fluid to the outside.

Reference numeral 1116 indicates an adjustment unit. Adjustment unit 1116 is comprised of a computer, a server, a cloud server, etc., and is connected to blood volume measurement unit 1113 via an electric lead 1113a to input blood volume data thereto. Further, adjustment unit 1116 is connected to blood pressure measurement unit 1117 via an electric lead 1117b to input blood volume data to adjustment unit 1116. Further, adjustment unit 1116 is connected to blood flow measurement unit 1118 via an electric lead 1118b to input blood flow data to adjustment unit 1116. Reference numeral 1116a indicates a manual operation input part, which is comprised of a button switch, a rotary dial, etc., and a doctor, nurse, etc., manually inputs signals for driving water removal means 1115 or to perform dialysis operations, such as reading a pattern from storage means 1114 and setting a water removal pattern.

Adjustment unit 1116 includes a computer as well as a robotic manipulator and a robotic type for performing a water removal amount adjustment drive and a water removal rate adjustment drive for water removal means 1115, and may comprise a drive manipulator for physically operates water removal means 15.

Reference numeral 1117 indicates a blood pressure measurement unit. Blood pressure measurement unit 1117 is comprised of an existing blood pressure monitor, a blood pressure related value measurement device such as a PWTT value measurement device, an upper arm cuff, an optical sensor for a fingertip, an electrocardiograph, a pulse wave estimation device, etc. The blood pressure sensor attached to the patient is input from blood pressure input terminal 1117a, and blood pressure data is formed at a predetermined interval (every 10 minutes, etc.), preferably in real time, and the blood pressure data is output to adjustment unit 1116 via electric lead 1117b.

Figure 12A:
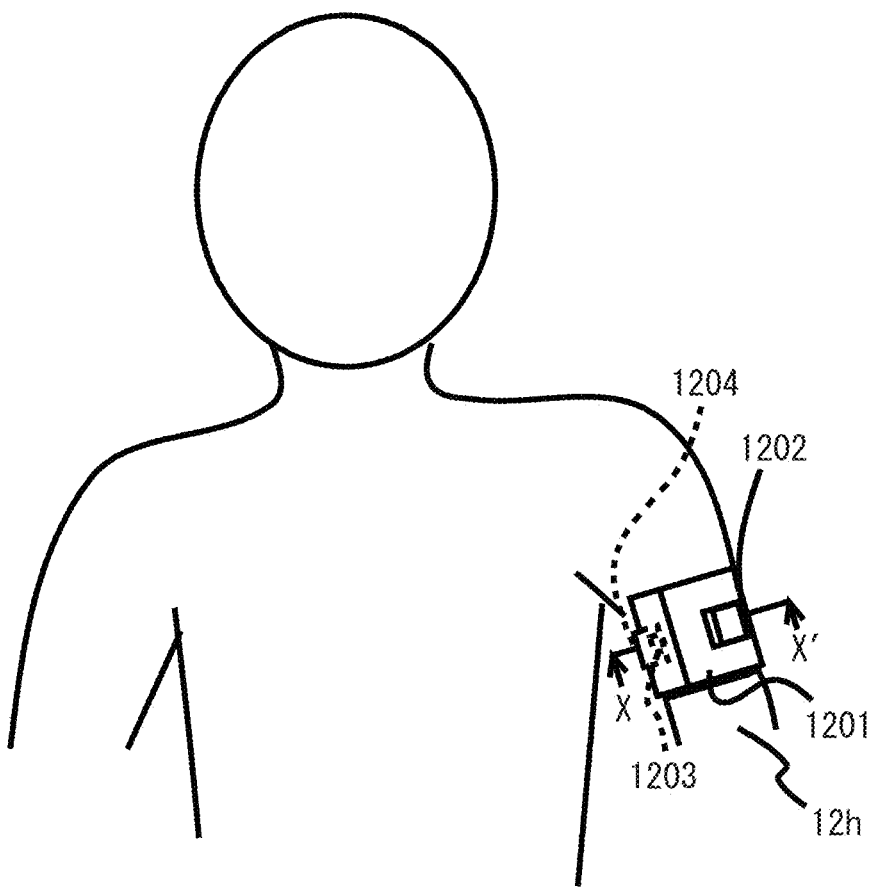
FIGS. 12A to 12C are views for illustrating another embodiment of the present invention.
Figure 12B:
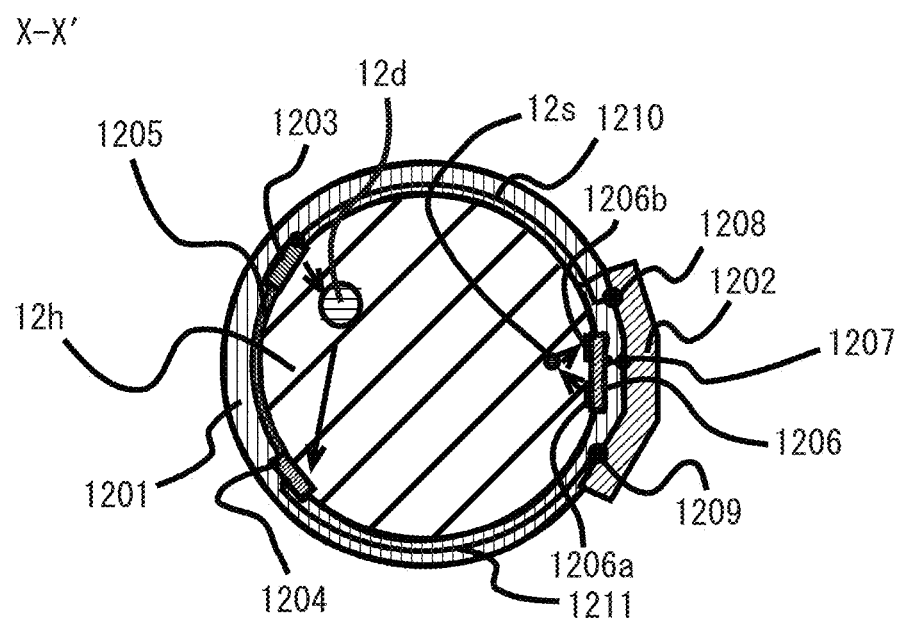

A specific example of blood pressure measurement unit 1117 will be described with reference to FIGS. 12A and 12B. FIG. 12A shows a continuous blood pressure measurement unit in the state of being wrapped around and worn on upper arm 12h. FIG. 12B is a sectional view taken along line X-X' of FIG. 12A. A pulse wave sensor using an LED having a wavelength (500 to 570 μm) represented by green color as a light emitter for detecting an arterial wave at a superficial part of the living body, and a pulse wave sensor using an LED having a wavelength (830 to 945 nm) represented by infrared light as a light emitter for detecting an arterial wave at a deep part of the living body are used. In FIG. 12A, reference numeral 1201 indicates a strip. Strip 1201 is formed of a vinyl or plastic material, or cloth, for surrounding a living body, such as a supporter, and is fixed at that position. Strip 1201 is configured to have stretchability with a flexible resin, cloth, or the like. For example, the upper arm is pressed from the surroundings by the stretchability of strip 1201, but the force is preferably such that the sensor in strip 1201 does not move. The width of strip 1201 is, for example, about 4 to 6 cm, and preferably 4.5 to 5.5 cm. However, the width is not limited to this value as long as pulse waves can be suitably detected.

Reference numeral 1202 indicates a housing. Housing 1202 is formed of a plastic material, metal, etc., and contains an antenna for wireless communication, an electric circuit board, a battery, etc. Housing 1202 includes a blood pressure measurement unit 1117 comprising a computer unit, shown in FIG. 11, and data can be transmitted to adjustment unit 1116 by WiFi. Further, a transmitter/receiver electronic circuit module for infrared light, WiFi, and Bluetooth™ is built into housing 1202 to transmit pulse wave electrical signals obtained from the light receiving section that detects green light and infrared light to the outside in a wireless form. Reference number 1203 indicates an infrared (IR) light emitting part. Infrared (IR) light emitting part 1203 is comprised of an LED, light emitting diode, etc., that outputs infrared light at a wavelength of 850 nm, and measures the blood flow of deep artery 12d of the upper arm.

Reference numeral 1204 indicates a light receiving part for infrared (IR) light. Light receiving part 1204 for infrared (IR) light is comprised of a phototransistor, a photodiode, etc. Reference numeral 1205 indicates a black sheet. Black sheet 1205 is made of a black rubber, resin, or sheet material having plastic flexibility, and removes light other than that transmitted through the body between infrared (IR) light emitting part 1203 and light receiving part 1204 for infrared (IR) light. Reference numeral 1206 indicates a sensor unit for green light. The sensor unit 1206 for green light is comprised of a green (G) light emitting part 1206a and a green (G) light receiving part 1206b. The green light output to the body 4h is reflected by a thin artery 12s, and the reflected light is received by green (G) light receiving part 1206b.

Reference numeral 1207 indicates an electrical connection part for green light. Electrical connection part 1207 for green light is comprised of an electric lead, a connector, etc., and is for supplying an electrical signal to green (G) light emitting part 1206a, and for transmitting an electrical signal of reflected light from green (G) light receiving part 1206b to a circuit within housing 1202. Reference numeral 1208 indicates an electrical connection part for infrared light emission. Electric connection part 1208 for infrared light emission is comprised of an electric lead 1210 for outputting infrared light, a connector, etc., and is a conductive connection part for electrical output to infrared (IR) light emitting part 1203.

Reference numeral 1209 indicates an electric connection part for infrared transmitted light. Electrical connection part 1209 for infrared transmitted light is comprised of an electric lead 1211 for transmitting an infrared light reception signal, a connector, etc., and is a connection part for transmitting an infrared light transmission electrical signal output by infrared (IR) light receiving part 1204 to housing 1202. Reference numeral 1210 indicates an infrared light output electric lead for transmitting an electrical output to the infrared light emitting part. Electric lead 1210 is for electrically connecting electric connection part 1208 for infrared light emission and infrared (IR) light emitting part 1203. Reference numeral 1211 indicates an electric lead for infrared light reception signal for transmitting an electrical output from the infrared light receiving part to housing 1202. Electric lead 1211 is for electrically connecting electric connection section 1208 for infrared light emission and infrared (IR) light emitting part 1203.

The operation of the embodiment shown in FIG. 12A will be described below.

Strip 1201 is formed in a cylindrical shape with stretchability, such as a supporter, and is worn around either the left or right upper arm of a human as shown in FIG. 12a. It is preferable that the infrared pulse wave sensor comprising infrared (IR) light emitting part 1203 and infrared (IR) light receiving part 1204 is mounted so that it is positioned on the armpit side in view of detecting pulse waves of deep thick artery 124d in a transmissive manner. However, depending on the condition of the patient's arteries, the infrared (IR) light emitting part 1203 and the light receiving part 1204 for infrared (IR) light may be arranged at the lateral side of the upper arm.

In housing 1202, an electrical circuit for transmitting and receiving the LED light reception signal to and from the outside by wireless via WiFi, infrared, etc., or by wire, is formed, realizing so-called IoT, and the housing also includes a battery unit such as a button battery. The start of use is carried out by turning on a switch provided in the aforementioned electrical circuit, or by turning on a membrane switch or the like, which is switched on simultaneously with mounting. When the electrical circuit in housing 1202 is turned on, the electrical circuit in housing 1202 supplies electrical signals to infrared (IR) light emitting part 1203 via electric leads 410.

Figure 12C:
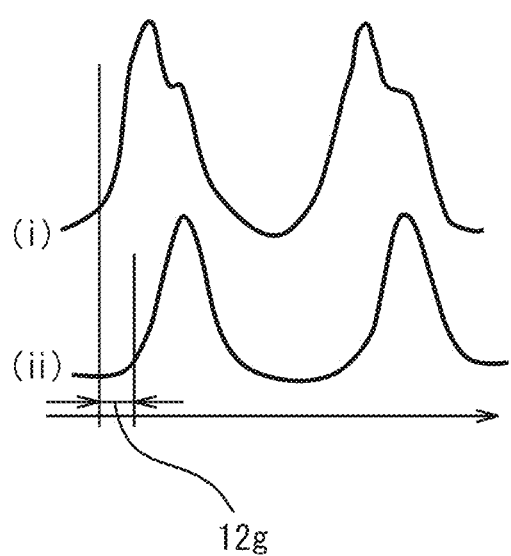

Infrared (IR) light emitting part 1203 outputs infrared light having a wavelength as described above. The light passes through the thick deep artery and is received by infrared (IR) light receiving part 1204. The light reception signal is converted into an electrical signal and supplied to an electrical circuit in housing 1202 via electric lead 1211. This electrical signal is transmitted via an antenna connected to an electrical circuit in housing 1202 to an operation terminal 1205, etc., shown in FIG. 12, including operation terminal 1205 equipped with circuits indicated by reference numerals larger than this number, including a green pulse wave second order differentiation means shown in FIG. 11.

Green (G) light emitting part 1206a of green light sensor unit 1206 irradiates a peripheral blood vessel 12s (22 in FIG. 13B) with green light, and then green (G) light receiving part 1206b receives the light. The received light signal is converted to an electrical signal, and a green pulse wave electrical signal is output to housing 1202. In the absence of circuits indicated by reference numerals larger than 1205, including a green pulse wave second order differentiation means, as shown in FIG. 1, the received pulse wave signals 01 and 02 shown in FIG. 13A are sampled by an AD converter, for example, in 0.01 to a few seconds, then converted to digital numeric data and transmitted to the outside. At the operation terminal 805, the input digital data is restored, and after forming an analog signal, second order differential processing is applied thereto.

Alternatively, if there is a second order differential analog circuit within the housing 1202, the second order differential signal may be sampled and transmitted to operation terminal 805, and in this case, the blood pressure related values and blood pressure value can be calculated quickly. Since the blood pressure value is an estimated value and may be at least an amount of variation, it is sufficient to find the time difference (phase difference) between the time phase of the rise of a pulse wave detected from the artery at a deep position of the living body and the time phase of the rise of a pulse wave detected from the artery at a superficial position from the skin of the living body (change in 12g in FIG. 12C). The variation in phase difference can indicate the rise and fall of blood pressure (PWTT is an electrocardiogram and pulse waves, but since the timing of the pulse waves of the thick artery at a deep part of the body is almost identical to the electrocardiogram signal, it can be approximated as the difference in phase difference between the pulse waves of the thin artery in a superficial position and a thick artery at a deep position).

Reference numeral 1118 indicates a blood flow measurement unit. Blood flow measurement unit 1118 is comprised of a laser blood flowmeter capable of measuring deep blood flow or other blood flow measurement devices. Sensor probes are fixedly placed on the patient's extremities, head, earlobes, and other areas where blood flow can be detected. Blood flow signals obtained from the sensor probes are input from the blood flow input end 18a, and after blood flow velocity, blood flow rate, etc., are calculated by the blood flow measurement unit, the signals are output to adjustment unit 1116 via electric lead 18b.

In place of electric leads 1113a, 1117b, and 1118b shown in FIG. 11, for example, wireless connection by a wireless operation unit (ZigBee, etc.) of WiFi, Bluetooth® connection may be used.

Next, the operation of the embodiment shown in FIG. 11 will be described with reference to FIG. 11. A blood access site is formed by puncturing and fixing blood removing part 1110a and blood returning part 1110b to a blood vessel using a hollow needle in the vicinity of upper arm portion 1110 having a shunt part provided for performing dialysis treatment. Extracorporeal blood circuit 1100 is formed between blood removing part 1110a and blood returning part 1110b of the blood access site.

Next, an appropriate water removal pattern is selected from the patient's treatment history data read from storage means 1114 by operating adjustment unit 1116, the blood pressure data input from blood pressure measurement unit 1117, the blood flow data input from blood flow measurement unit 1118, and from the water removal patters in FIGS. 3C and 3D at the time of starting an appropriate treatment and other predetermined water removal patterns. This selection is made by a doctor, nurse, clinical technician, or when there is a large amount of data, or may be determined predictively by the application to a corresponding data obtained in advance by a machine learning process or deep learning process such as neural network based on the patient's data (such as body temperature data, body weight data, water removal rate data, etc.) during previous dialysis treatment. The corresponding data in this case is the data including the blood pressure stable boundary obtained after ensemble learning by creating a decision tree with body temperature data, BODY weight data, and water removal rate data as explanatory variables and blood pressure stable state (maximum fluctuation range of blood pressure) data during dialysis treatment as a selection variable, and when patient data such as body temperature data is input, the blood pressure stable state is uniquely indicated.

In adjustment unit 1116, when a pattern of water removal for the patient is set and a dry weight and others are input, and a specific water removal speed is set, it starts a dialysis treatment with the water removal rate of the pattern as shown in FIG. 13C or 13D, for example. The blood flowing through blood circuit 1100 is transported to dialyzer 1112 where the wastes and body fluid that have permeated to the outside of the hollow fibers due to difference in concentration are transported by a buffer solution and transported to water removal means 1115, and the water removal valve (not shown) is opened at a setting corresponding to the water removal rate set by the output signal of adjustment unit 16 to discharge the body fluid to the outside.

Blood volume measurement unit 1113 detects the blood volume (BV value) in blood circuit 1100 and calculates the PRR value from the blood volume. The PRR (plasma refilling rate) value is a ratio (velocity) of a body fluid in the body fluid that enters a blood vessel from outside the blood vessel and is an estimated value calculated from a BV meter, etc. For example, the variation in the PRR value is shown by a solid line in figures. When the rate of decrease in the PRR value becomes equal to or more than a predetermined value, adjustment unit 1116 drives water removal means 1115 to reduce the water removal rate and narrow the opening area of a water removing drive valve.

Conversely, when the rate of increase in the PRR value is equal to or greater than a predetermined value, adjustment unit 1116 drives water removal means 1115 to increase the water removal rate by increasing the opening area of the water removing drive valve. The predetermined value of the PRR value may be set in advance based on the dialysis history data of the patient and individual differences of the patient. In the case of manual operation, the variation in the PRR value may be set as a measure while observing the variation in the PRR value with a computer monitor, etc. The predetermined value is determined depending on the individual difference of the patient, but, for example, it may be a value in a case where the water removal rate is adjusted under a condition where the rate of variation in the blood pressure value measured at the same time is small. The predetermined value is set as a threshold. However, since the predetermined value is based on the individual differences of the patient, the predetermined value may be included in the patient data as an objective variable, and a decision tree, random forest, or other process may be used to create a predetermined value that stabilizes the blood pressure as the corresponding data in advance. Further, it is not necessary to calculate the PRR value, but the blood concentration value may be measured and may be used as a measure for determining that the water removal is excessive when the concentration is higher than a predetermined value, which improves the accuracy over an estimated value.

The blood pressure of the patient over time can be input from blood pressure input terminal 17a to blood pressure measurement unit 1117 and blood pressure measurement unit 1117 can monitor whether the blood pressure is stable. When the variation in the blood pressure reaches to a predetermined value or higher, blood pressure measurement unit 1117 outputs a signal to that effect to adjustment unit 1116. The blood flow of the patient over time can be input from blood flow input terminal 1118a to blood flow measurement unit 1118 and blood flow measurement unit 1118 can monitor whether the blood flow is stable. When the variation in the blood flow reaches to a predetermined value or higher, blood flow measurement unit 1117 outputs a signal to that effect to adjustment unit 1116. When the blood pressure value reaches to a predetermined value or higher, an operation to reduce the water removal rate of water removal means 1115 may be instructed even if the rate of decrease in the PRR value output from blood volume measurement unit 13 is equal to or less than a predetermined value.

Further, for example, when the blood flow value in the brain and the blood flow value in the neck differ by more than a predetermined value, an operation to decrease the water removal rate of water removal means 1115 may be indicated even if the rate of decrease in the PRR value output from the blood volume measurement unit 1113 is equal to or less than a predetermined value. In this way, the water removal rate is adjusted according to the variation in the PRR value calculated from blood volume measurement unit 1113, and when the blood pressure measurement value of blood pressure measurement unit 1117 exceeds a predetermined value or when the difference between the blood flow values of the respective parts output from blood flow measurement unit 118 reaches to a predetermined value or higher, the patient can receive adequate dialysis treatment under stable blood pressure.

Figure 13:
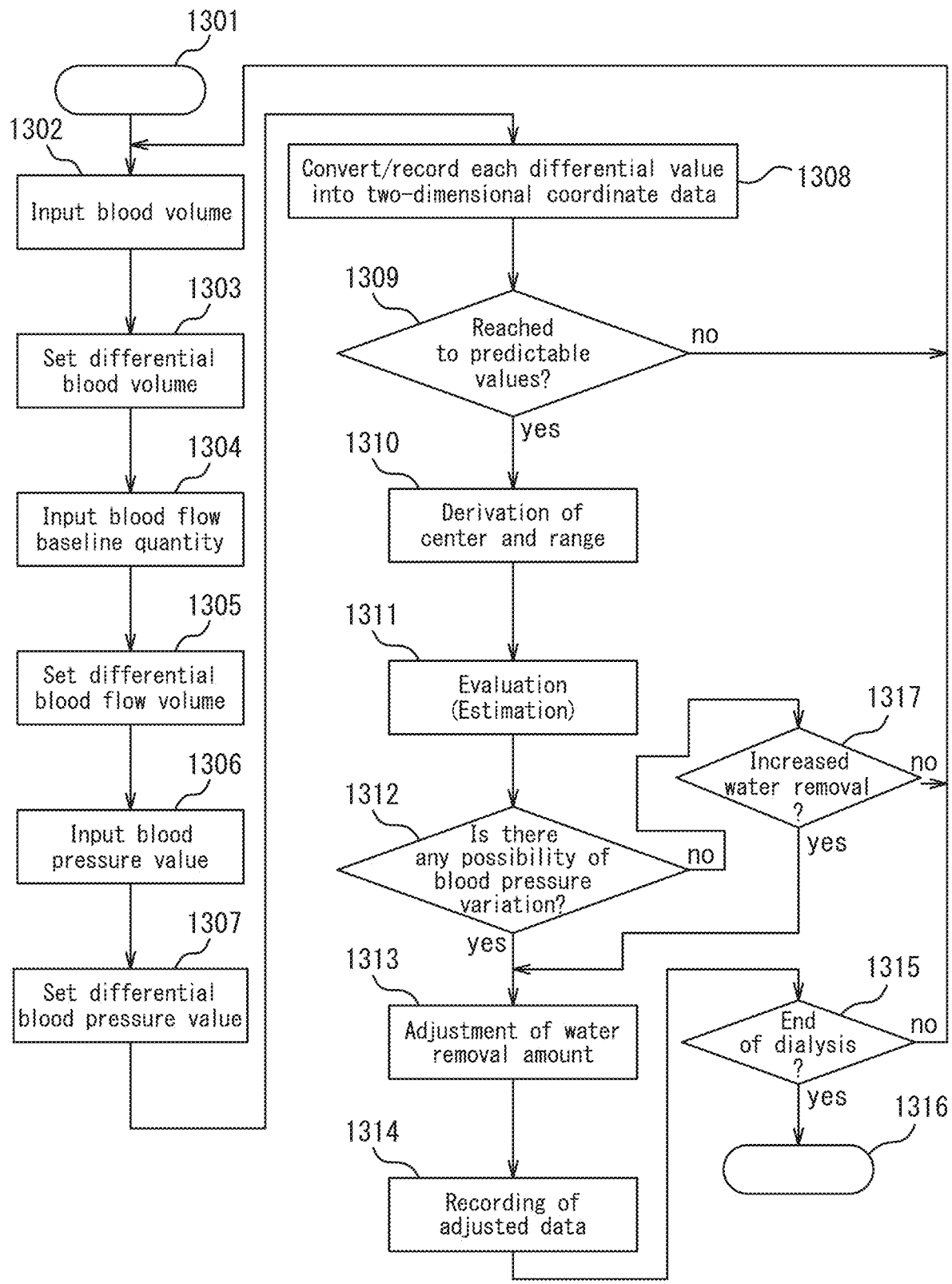
FIG. 13 is a diagram for illustrating another embodiment of the present invention.

Next, another example of the present invention will be described in detail with reference to FIG. 13. FIG. 13 shows a flowchart, which is stored in storage means 1114 as a program of adjustment unit 1116 comprising the computer shown in FIG. 13, is loaded into the computer, and is executed. The flowchart shown in FIG. 13 is an example of a machine learning program that uses a clustering method in artificial intelligence, and is composed of, for example, a Python program using the Scikit-Learn module, etc. Only the main part of the program function is shown. For example, the program code shown in FIGS. 15A-15B is a part of a clustering process in which 100 variations in blood pressure data and blood flow data are sent each time from the outside, i.e., blood flowmeter and sphygmomanometer, in CSV file format, and are displayed as two-dimensional graphs and time-series three-dimensional data for learning 300 times with three centroids.

Step 1301 is a start step, step 1302 is a step of obtaining a blood volume and a PRR value by blood volume measurement unit 1113 shown in FIG. 1, and step 1303 is a step of calculating the differential values for the PRR value or blood volume obtained in step 1302 and conducting arithmetic processing by a computer of adjustment unit 1116.

Step 1304 is a step of obtaining the blood flow data obtained from the patient's head, neck, hands, feet, etc., with blood flow measurement unit 1118 shown in FIG. 11. The blood flow measurement probe or sensor to be connected to 1118a of blood flow measurement unit 1118 may be worn on the head or placed and fixed near the shunt, near the heart, etc., if it irradiates near-infrared light and obtains a blood flow from the reflected wave. Step 1305 is a step of obtaining a blood flow differential value from the blood flow data obtained in step 1304, and conducting arithmetic processing by a computer of adjustment unit 1116.

Step 1308 is a step of forming each differential value as two-dimensional coordinate data. It is a step of extracting differential value blood volume data, differential value blood flow data, and differential value blood pressure data of the same time for a predetermined period of time (from tens of seconds to tens of minutes) and converting them into coordinate data, for example, so that the horizontal axis is differential value blood volume data and the vertical axis is differential value blood pressure data, or so that the horizontal axis is differential value blood flow data and the vertical axis is differential value blood pressure data.

Step 1309 is the step of judging whether the predetermined period has elapsed or the amount of data has reached a predictable state, and the amount of coordinate values, or another cluster, if it occurs, sets the data up to that point as one predetermined period. In other words, if the number of clusters exceeds the preset number of clusters, the evaluation may be changed to the next predetermined period, in which case, the preset number of clusters may be changed corresponding to the number of predetermined periods since the start of dialysis. By combining the two-dimensional coordinate data of the predetermined period with the z-axis as time, the time-series changes in blood pressure, blood flow, and blood volume are shown, and the prediction of blood pressure fluctuations after a long time becomes possible.

Step 1310 is a step of deriving the feature points and feature ranges. The feature point indicates the centroid in the case of clusters, and the feature range indicates the range of a single cluster, which is determined through repeated calculations while changing the center coordinates so that the Euclidean distance from the centroid coordinates is the shortest. 1311 is the step of evaluation and prediction. For example, if the horizontal axis is the blood flow differential value and the vertical axis is the blood pressure differential value, and the coordinate of the centroid is the center, and the range of clusters accumulates at the center of the coordinate, this coordinate value approximately evaluates the degree of variation in intravascular volume and sets the possibility of blood pressure fluctuations.

Step 1312 is a step of receiving the evaluation result of step 1311 and determining the possibility of fluctuations in blood pressure. Step 1313 is a step in which adjustment unit 1116 shown in FIG. 1 outputs a signal for reducing the water removal rate to water removal means 1115 when there is a possibility that the blood pressure may fluctuate. Step 1314 is a step of recording the adjustment of the water removal rate with time, storing the evaluation contents, etc., in step 1311, and forming historical data of the water removal operation and storing it in storage means 1114 shown in FIG. 11 as patient data. The data stored in this storage means is used for selection of the initial water removal rate pattern shown in FIG. 19, etc., and may be recorded and registered so as to be usable as big data by an external cloud computer. Step 1315 is a step of confirming the end of dialysis, and step 1316 is the end step. Step 1317 is a step of examining the possibility of an increase in the amount of water removal, and, for example, in the relationship between the PRR value and the water removal rate shown in FIG. 19(*e*), whether the PRR value is at an elevated timing is calculated based on the circulating blood flow rate, and the timing is checked to see if the variation direction of the blood flow and the variation direction of the blood flow match with each other, and if both directions match with each other, a control signal to increase the amount of water removal by 10% on a trial basis and an alarm signal are generated. Then, if the PRR value is constant, but the blood flow further decreases and the blood pressure shows a tendency to increase, it is assumed that the load of vasoconstriction has increased further, and it moves to 1313 in which an adjustment to reduce the water removal amount is performed. As described above, by performing control to increase the amount of water removal, it is possible to perform water removal without difficulty for the patient, and dialysis efficiency can be improved.

Next, the operation of the embodiment shown in FIG. 11 will be described with reference to FIG. 13. FIG. 13 shows a step subsequent to the step of selecting a water removal pattern according to the individual difference in the embodiment shown in FIG. 11. In some cases, the steps shown in FIG. 13 alone can be used as an embodiment of the invention without requiring the step of selecting a water removal pattern according to individual differences. Adjustment of the water removal rate based on the PRR value is only a minimum adjustment, and an operation to complete the target water removal within a predetermined time while performing an adjustment to increase or decrease the water removal amount based on the variation of the blood pressure data and the blood flow data. After the start of dialysis (Step 1301), blood volume measurement unit 1113, blood pressure measurement unit 1117, and blood flow measurement unit 1118 shown in FIG. 1 input the blood volume, blood flow rate, and blood pressure values and form the respective differential data as shown in steps 1302, 1304, and 1306 in FIG. 13 (Steps 1303, 1305 and 1307). The differential values are at least for making the obtained biological signals coordinateable in two or more dimensions, and are not particularly limited, and they may be for other transformation as long as a relationship having regression and correlation is formed.

All of these difference values are converted to values that can be coordinated on the same two-dimensional coordinates. Next, this differential value data is converted into two-dimensional coordinate data for a predetermined period of time, for example, with the blood differential value on the horizontal axis and the blood pressure differential value on the vertical axis at the same time (Step 1308). Furthermore, two two-dimensional coordinate data is formed with the blood flow differential value as the horizontal axis and the blood pressure differential value as the vertical axis, or with the blood flow differential value as the horizontal axis and the blood differential value as the vertical axis.

If this coordinate data is performed at predetermined time intervals, or if the coordinate values suddenly become distant values and remain distant continuously, it is determined that prediction of blood pressure variation is possible based on the previous coordinate values, and feature points and feature ranges are derived in step 1310. In step 1310, fluctuations in blood pressure is predicted and evaluated from the obtained feature points (centroid) and the range of one cluster (feature range). For example, when the horizontal axis is the blood flow differential value and the vertical axis is the blood pressure differential value, the coordinates are considered to be related to the degree of change in the intravascular volume. Thus, if the coordinates are close to the origin and a cluster is formed in the range close to the origin, it indicates the possibility that the vascular resistance is large and trying to stabilize the blood pressure, and it is judged that the probability that further water removal will cause a sudden drop in blood pressure has increased (Step 1312) (Yes), and adjustment unit 1116 operates water removal means 1115 to reduce the water removal rate and decrease the amount of water removal (Step 1313).

When the water removal amount is adjusted, the water removal amount is recorded in the adjustment data together with the time information from the start of the dialysis treatment in storage means 1114. If there is no possibility of fluctuations in the blood pressure (Step 1312) (No), the blood pressure data and the blood flow data are referred to whether the water removal amount can be increased. If the blood pressure data and the blood flow data are within the permissible range for water removal and there is room to increase the amount of water removal, the increase in the amount of water removal is adjusted (Step 1313). In Step 1317, if there is no room to increase the amount of water removal (No), the system returns to the blood volume input step (1302) again and performs a data input operation. When the dialysis time is finished (Step 1315) (Yes), the dialysis treatment ends (Step 1316).

As explained above, by converting each differential data into two-dimensional coordinates and performing correlation or regression processing, it may be possible to predict the point in time when blood pressure fluctuations can be adjusted in advance. If the number of clusters increases within a predetermined time range, or if the range of clusters has a tendency to fluctuate in dispersion, it indicates that the blood pressure is fluctuating significantly, and adjustment unit 1116 may reduce the water removal rate of water removal means 15 and also supply supplementary fluid to blood circuit 1100.

In addition, by listing the data before dialysis treatment obtained based on the relationship between the blood pressure and the blood flow described above, the time from the dialysis start time, the water removal amount, the number of clusters, the coordinates of each centroid, the ranges of the clusters, and the evaluation items in a table to obtain data, individual patient patterns during dialysis treatment can be obtained. The evaluation items are set in five levels, for example, 5 is given when gentle dialysis treatment is performed to the patient, and 1 is given when the dialysis treatment is not gentle. In the intermediate cases, rules are made in advance and values are assigned according to the rules. These are recorded sequentially to form a database of the patient's dialysis treatment patterns, and are continuously recorded on a computer's hard disk, USB memory, server, etc.

The accumulation of the individual difference pattern data of the patient can be used as variable data for artificial intelligence programs such as random forests, neural networks, etc., creating the possibility of predicting and determining the optimal dialysis pattern using these set variables, and can be used as autopilot data for automated dialysis treatment. For example, prior to the start of dialysis treatment, the individual difference pattern data that corresponds to the data indicating the patient's weight and physical condition and that has a high rating of 4 to 5 is selected, and dialysis treatment is started at a water removal rate based on the pattern data. During dialysis treatment, clusters are detected in the time series, and the centroid and the range of clusters are compared with the selected individual difference pattern data, and if they are similar, the amount of water removed is adjusted within the allowable range of the water removal rate of the individual difference pattern data. If they are not similar, the autopilot is stopped, the data of the stop is appended to the individual difference pattern data, and only the individual difference pattern data during treatment is recorded, and dialysis treatment based on time-series prediction is performed.

Next, another example of the invention will be described in detail with reference to FIG. 14. Reference numeral 1401 denotes a dialysis machine. An example of dialysis machine 1402 is an existing dialysis machine, such as an HD or HDF type dialysis machine. Reference number 1401a indicates a blood pump for circulating blood removed from the body through dialysis machine 1401 and dialyzer 1402. Blood pump 1401a can be a rotary pump. Reference numeral 1401b indicates a blood tube A for transporting blood from the body to dialyzer 1402 via a blood removing part. Blood passes through the inside of blood tube A. Blood tube A is formed of a transparent and translucent resin. Reference numeral 1401c indicates blood tube B for returning blood from dialyzer 1402 to blood removing part 1412b.

Reference numeral 1402 indicates a dialyzer (dialysis machine). Dialyzer 1402 can be an existing off-the-shelf product with the sides of its housing section formed of a transparent or translucent material. Reference number 1403 indicates a laser blood flowmeter. An example of a laser blood flowmeter 1403 is a Doppler laser blood flowmeter, preferably a laser Doppler blood flowmeter that can measure over a wide frequency range (about 150 KHz to about 500 KHz). Reference numeral 1403a indicates the blood flowmeter probe for dialyzer. Blood flowmeter probe 1403a for dialyzer is comprised of an irradiating section that irradiates laser light and a light receiving section that receives laser light from the irradiation section. In the case of reflective measurement, the irradiating section and the light receiving section of probe 1403a may be arranged so that they face each other at a predetermined angle. In the case of transmission measurement, the two probe units (irradiator and receiver) may be fixed so that they face each other on the sides of dialyzer 1402. Reference numeral 1403b indicates a transmission member A. Transmission member 1403b is formed of an optical fiber or an electric lead and is used to transmit the light received by the blood flowmeter probe or the photoelectrically converted electrical signal to the laser blood flowmeter.

Reference numeral 1403c indicates a patient blood flowmeter probe. Patient blood flowmeter probe 1403c has a reflection type configuration in which an irradiating section that irradiates a laser beam and a reflection return section to which the reflection by the tissue in the skin is returned are arranged at a predetermined angle. When the patient's blood flowmeter probe 1403c measures, for example, an earlobe or the like, it has a light-emitter on one side and a light receiver on the other side. Reference numeral 1403d indicates a transmission member B by an optical fiber, an electric lead, or the like. As transmission member 1403, a transmission cable for a blood flowmeter attached to patient 1406 is exemplified. Reference numeral 1403e indicates an electric transmission path. Electric transmission path 1403e is a wire cable such as a LAN cable, USB cable, etc., or a transmission path for transmitting a medium such as WIFI, infrared radiation, and Bluetooth®.

Reference numeral 1404 indicates a continuous sphygmomanometer. Continuous sphygmomanometer 1404 detects the pulse waves at a deep position and the pulse waves at a superficial position under the strip worn on the upper arm, as shown in, for example, FIG. 6, and calculates blood pressure values based on the difference between them. Continuous sphygmomanometer 1404 conducts an estimated measurement for blood pressure value, based on, for example, the method described in Japanese Patent Application No. 2019-35914. It is not necessary to calculate the blood pressure value, but the amount of variation thereof may be calculated. Since the amount of variation is a relative value, the first reference blood pressure value may be measured in some cases.

Laser blood flowmeter 1403 and continuous sphygmomanometer 1404 each has a data output unit to which a computer unit having an OS (operating system) such as WINDOWS®, linux, MACOS, etc., is connected, and has a WiFi, Bluetooth®, or infrared transmitting/receiving module. The operating system comprises a data output unit for data sharing and remote desktop connection, and a data input unit for converting an analog signal into a digital signal by an AD converter for processing. Reference numeral 1404a indicates a pressure-free cuff for wearing on upper arm. Pressure-free cuff 1404a for wearing on upper arm comprises an infrared light emitter, a green light emitter, a continuous projection for blocking light leakage from the outside when wound and mounted, an electrocardiogram electrode, a pneumatic bladder containing a heart sound sensor, etc. Reference numeral 1404b indicates a transmission path. The transmission path 1404b is formed of electric wire cable, wireless medium, etc., and is a for transmitting blood pressure value data, etc., obtained with the pressure-free cuff for wearing on upper arm to the continuous blood pressure monitor 1404, or for transmitting pulse wave signals and electrocardiogram signals for calculating blood pressure data when the data is processed in continuous sphygmomanometer 1404.

Reference numeral 1404c indicates a data transmission path. Data transmission path 1404c is formed of a USB cable, LAN cable, etc., and is a cable or wireless medium for transmitting blood pressure values to computer terminal 1405. Reference numeral 1405 indicates a computer terminal. Computer terminal 1405 is equipped with a storage device such as a hard disk, USB memory, etc., and a processing execution unit that executes based on a program stored inside. Computer terminal 1405 is also preferably equipped with a display monitor, a computer mouse, a keyboard, a touchpad, and a touchpad-type display monitor. Computer terminal 1405 executes the machine learning algorithm and deep learning algorithm described above as a program.

Reference numeral 1405a indicates a data transmission path for dialysis machine. Data transmission path 1405a for dialysis machine is comprised of WiFi, wireless LAN, wired LAN, infrared communication, Bluetooth®, etc., and is for transmitting data to dialysis machine 1401 or for remote operation. The reference number 1405b indicates the screen/audio output section. Examples of the screen/audio output section 1405b include a computer display and a sound generator such as a speaker or earphone. Screen/audio output section 1405b informs the physician, etc., by screen and audio, for example, when the blood pressure blood flow is not stable and the heart rate increases, or when a sudden change in blood pressure is likely to occur within ten minutes. For example, if the blood pressure blood flow is not stable and the heart rate increases, or if a sudden change in blood pressure is likely to occur within a dozen minutes, the screen/audio output section 1405b notifies a doctor and others of the same.

Reference numeral 1405c indicates a patient communication means. Patient communication means 1405c is a transmitter for screen/audio display to the patient, and is formed of wireless such as WiFi, infrared, Bluetooth®, or LAN cable. Reference number 1406 indicates a patient. On one of the patient's arms, there is formed a blood access section comprised of a blood removing part to supply blood to the dialysis machine and a blood returning part to return the purified blood obtained from the dialyzer to the body.

Reference number 1407 indicates a dialysis treatment worker, such as a doctor, nurse, or clinical engineer. Reference number 1408 indicates a dialysate circuit. Dialysate circuit 1408 includes a pump and has a configuration for flowing a dialysate from the bottom of the dialyzer upward through dialysate tubes 1408a, 1408b, as well as a configuration for discharging water and wastes to the outside. Replacement fluid supply section 1409 is a replenishment section for saline solution and necessary components that have been removed. Reference number 1410 indicates a control operation section. Control operation section 1410 has a configuration similar to a computer system including a display monitor, a computer mouse, a touchpad, a keyboard, CPU, GPU, etc.

Reference numeral 1411 indicates a water removal adjustment section. Water removal adjustment section 1411 is formed of an electrically controllable valve such as an electromagnetic valve, and performs an opening/closing operation, etc., by an external electric signal. Reference numeral 1412 indicates a blood access section. Blood access section 1412 includes a blood removal part that extracts blood from a vein in the vicinity of an internal shunt part that connects an artery and a vein with a puncture hollow needle, and a hollow needle punctured into a vein to return the blood purified by dialyzer 1402 to the body.

Next, an operation will be described. Pressure-free cuff 1404a is wrapped around the upper arm of the dialysis patient and fixed so that the patient does not feel any pressure and the sensor adheres to the skin. The pressure-free cuff for wearing on upper arm is preferably fixed so that it does not slip off and does not impose a burden on the patient.

Reference numeral 1404a is a pressure-free cuff for wearing on upper arm, which detects pulse waves of an artery at a deep position from the skin by an infrared pulse wave sensor and pulse waves of another artery at a position shallow from the skin by a green sensor. If it is difficult to detect the pulse waves of the artery at a deep position from the skin, it is preferable to use electrodes for measuring at least one induction of the electrocardiograph, for example, by attaching them to both arms or holding each electrode in place by a cuff, for example, across the heart.

The rise time phase signals of both the infrared pulse wave signal and the green pulse wave signal obtained by the pressure-free cuff 1404a for wearing on upper arm are transmitted to continuous sphygmomanometer 1404 via 1404b. Continuous sphygmomanometer 1404 is ultra-compact and may be housed and integrated into the pressure-free cuff 1404a for wearing on upper arm. The continuous blood pressure monitor 1404 further transmits data to the computer terminal 1405. In this case, the data may be processed in advance, for example, in batch-wise by measuring the data at sampling points (at an interval of 0.1 to 10 seconds) and converting the data into a CSV file, and, when a predetermined number of sampling points has been accumulated, transmitting the data to computer terminal 1405 or sharing a folder so that computer terminal 1405 detects and processes the files as they are accumulated in the folder in a batch processing format.

The blood flow data detected from blood flowmeter probe 1403c for patient mounted on the abdomen and limbs of patient 1406 is transmitted to laser blood flowmeter 1403 via transmission member B1403d. When transmission member B1403d is an optical fiber, the blood flow data is transmitted as reflected return light to laser blood flowmeter 1403, and when blood flowmeter probe 1403c for patient is comprised of a laser output chip and a light receiving semiconductor element, it is transmitted to laser blood flowmeter 1403. Laser blood flowmeter 1403 calculates a blood flow rate and a blood flow amount from the received signals, and outputs the calculated data to computer terminal 1405.

The reflected light or transmitted light are detected by blood flowmeter probe 1403a for dialyzer connected to dialyzer 1402, and are input to laser blood flowmeter 1403 via transmission member A1403b, and then converted into the target values for blood flow rate, blood flow amount, etc., and transmitted to computer terminal 1405. Computer terminal 1405 monitors blood flow data and blood pressure data over time. Their variations within a predetermined time are determined. Since blood flow data frequently fluctuates due to sympathetic nerve and skin stimulation, a baseline is extracted to clarify variations in blood flow due to water removal. The baseline is indicated by reference numeral 1603 in FIG. 16. This baseline is based on the tendency of the blood flow to decrease due to the amount of water removed. This baseline is obtained by detecting the lowest value that occurs in the time series of the blood flow waveform and connecting these values. After connecting the values, values are acquired at predetermined intervals, and the amount of variation at each sampling interval is acquired. Reference numeral 1601 indicates a blood pressure waveform. This waveform is based in part on a chart showing the variations in blood flow and blood pressure during dialysis treatment in Case 1 in the document (http://www.tokyo-hd.org/pdf/44th/44th 04_18.pdf Study on the usefulness of laser blood flowmeter).

Figure 16:
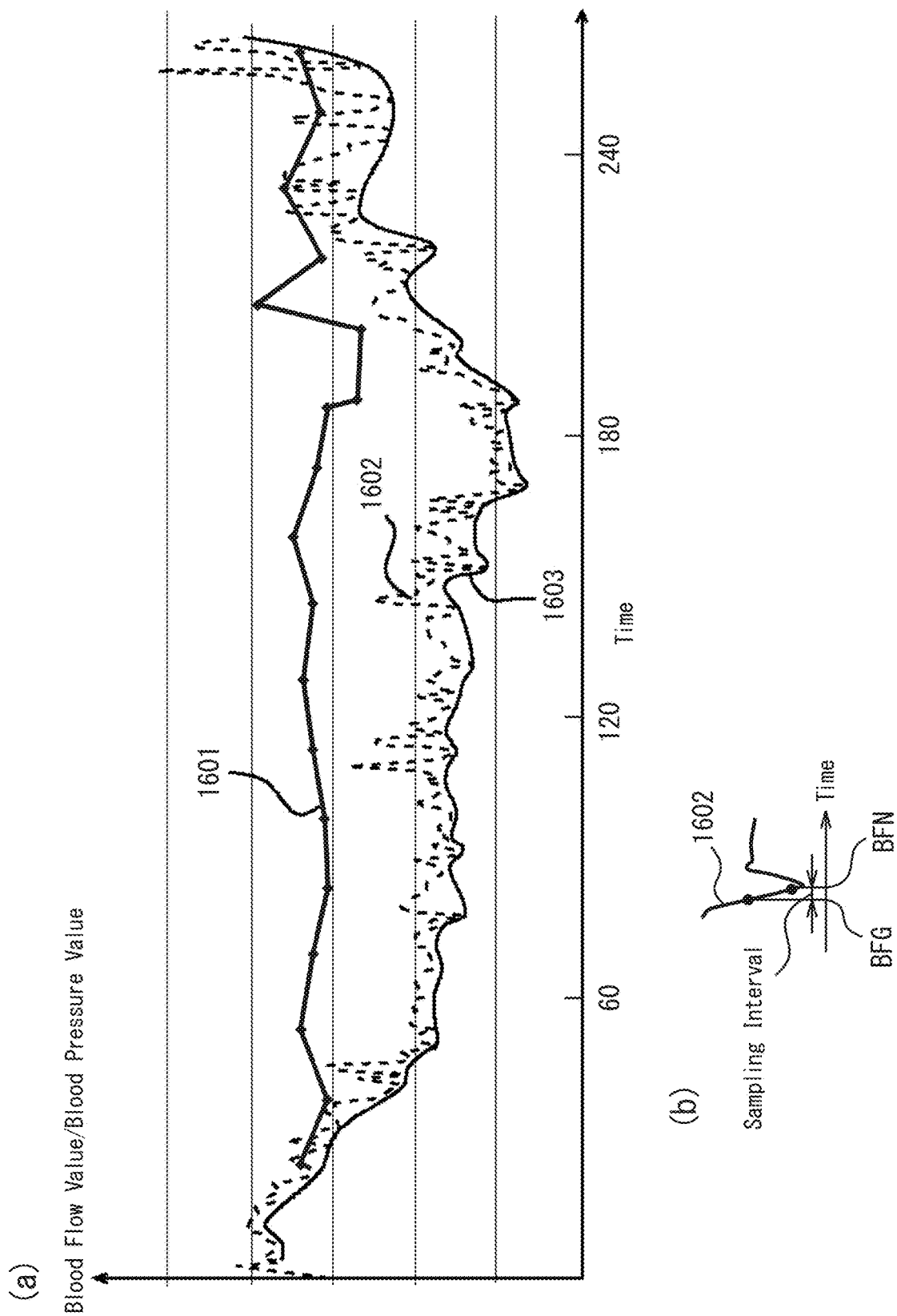
FIG. 16 is a diagram for illustrating another embodiment of the present invention.
Figure 17:
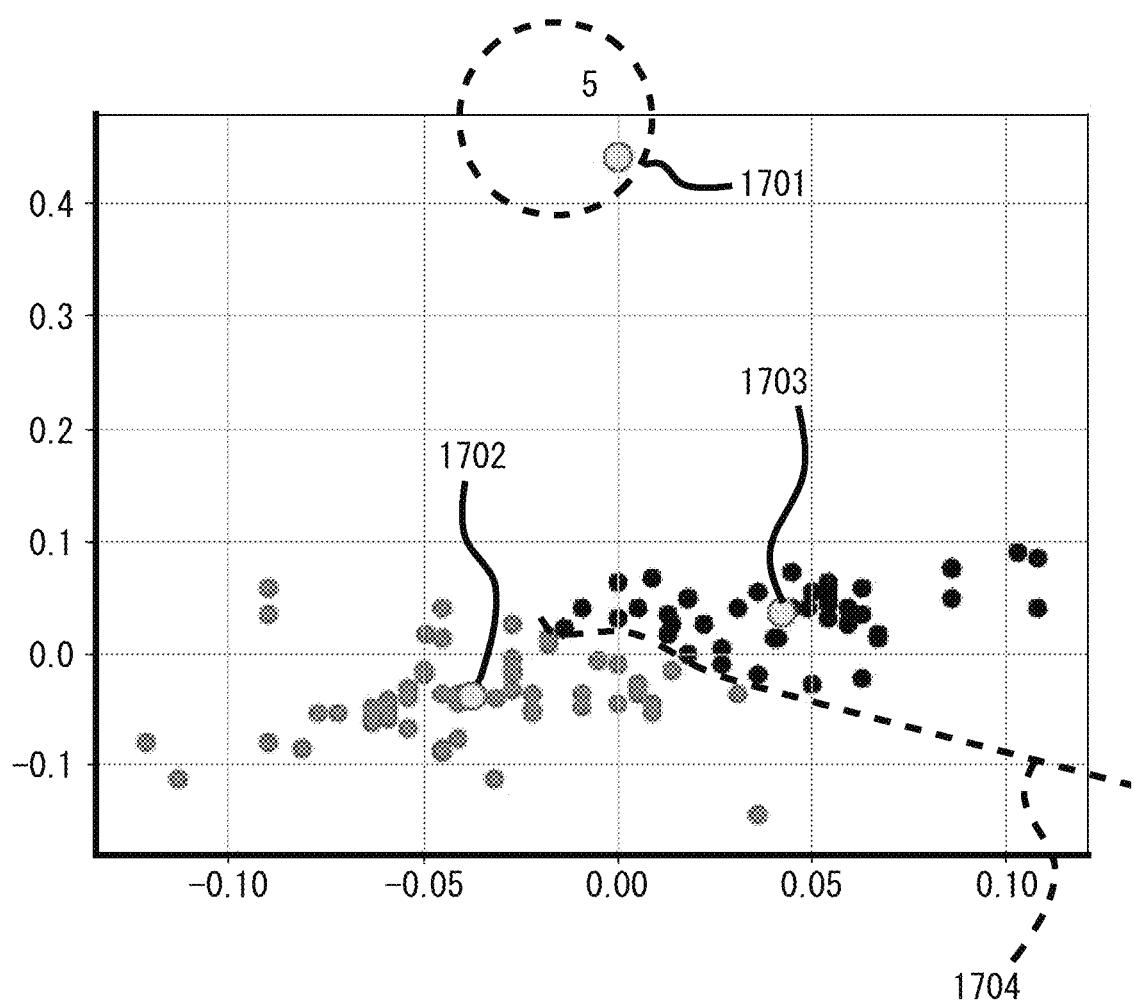
FIG. 17 is a diagram for illustrating another embodiment of the present invention.

While detecting the baseline as shown in FIG. 16, a two-dimensional chart with the change in blood flow on the horizontal axis and the change in blood pressure on the vertical axis is created for every 100 points, and the chart is divided into three regions by performing a machine learning process with clustering. Then, a centroid is determined for each of these regions, and the fluctuations in blood pressure are monitored while observing the variation of each centroid to achieve predictions. FIG. 17 shows the chart 60 minutes after the start of dialysis. The blood pressure and blood flow baselines shown in FIG. 16 were converted into coordinates using digitizer software, and then the digital signals based on these coordinates were converted into analog signals using a D/A converter to form simulated blood outflow and blood pressure outputs.

The blood flow output and the blood pressure output are respectively converted into digital signals by an A/D converter and coordinated, and then a blood pressure value and a blood flow value are detected at predetermined intervals, and while performing a clustering processing, the relationship between blood pressure and blood flow is made into a dispersion diagram for every 100 points, and the centroid(s) determined as a result of learning by the clustering process is extracted, and the variations thereof are monitored to predict the fluctuations in blood pressure. FIGS. 15A to 15B show a part of the program code created by Python 3.6. Into the program code of FIGS. 15A to 15B, the following program code was imported, and a clustering process using Kmeans was performed:

"import numpy as np
from sklearn. cluster import KMeans
from sklearn. decomposition import PCA
import matplotlib. pyplot as plt"

FIG. 17 shows an example of the dispersion diagram. In FIG. 17, the vertical axis is the amount of variation in blood flow and the horizontal axis is the amount of variation in blood pressure. It is 30 minutes after the start of the measurement, which is the time when the blood pressure data started to be measured. Reference numerals 1701, 1702, and 1703 are the centroids and indicate the centroid values of the plotted blood flow and blood pressure values, respectively. The centroids indicated by reference numeral 1702 is a single plot. The reason for using three centroids is to further determine the center of these centroids and to trace the time series displacement of the center. The number of centroid(s) may be any number other than three. Reference numeral 1701 shows a single blood flow and blood pressure variation with only the centroid is shown. Reference numeral 1704 indicates a boundary where the two areas are divided by the program based on the result of learning 300 times. On the screen of a computer monitor, they are color coded. Four variation direction areas, i.e., (blood flow plus direction, blood pressure plus direction), (blood flow minus direction, blood pressure plus direction), (blood flow plus direction, blood pressure minus direction), and (blood flow minus direction, blood pressure minus direction) can be set for the states of blood flow and blood pressure, and therefore the two types of information can be easily viewed in one form, and by the centroid process, the tendency is processed into a form that is easy to read. For example, variations in reduction of blood flow and in increase of blood pressure during vasoconstriction can be confirmed within the range where the centroids are concentrated, and variations in vascular conditions can be confirmed based on time information.

Figure 14:
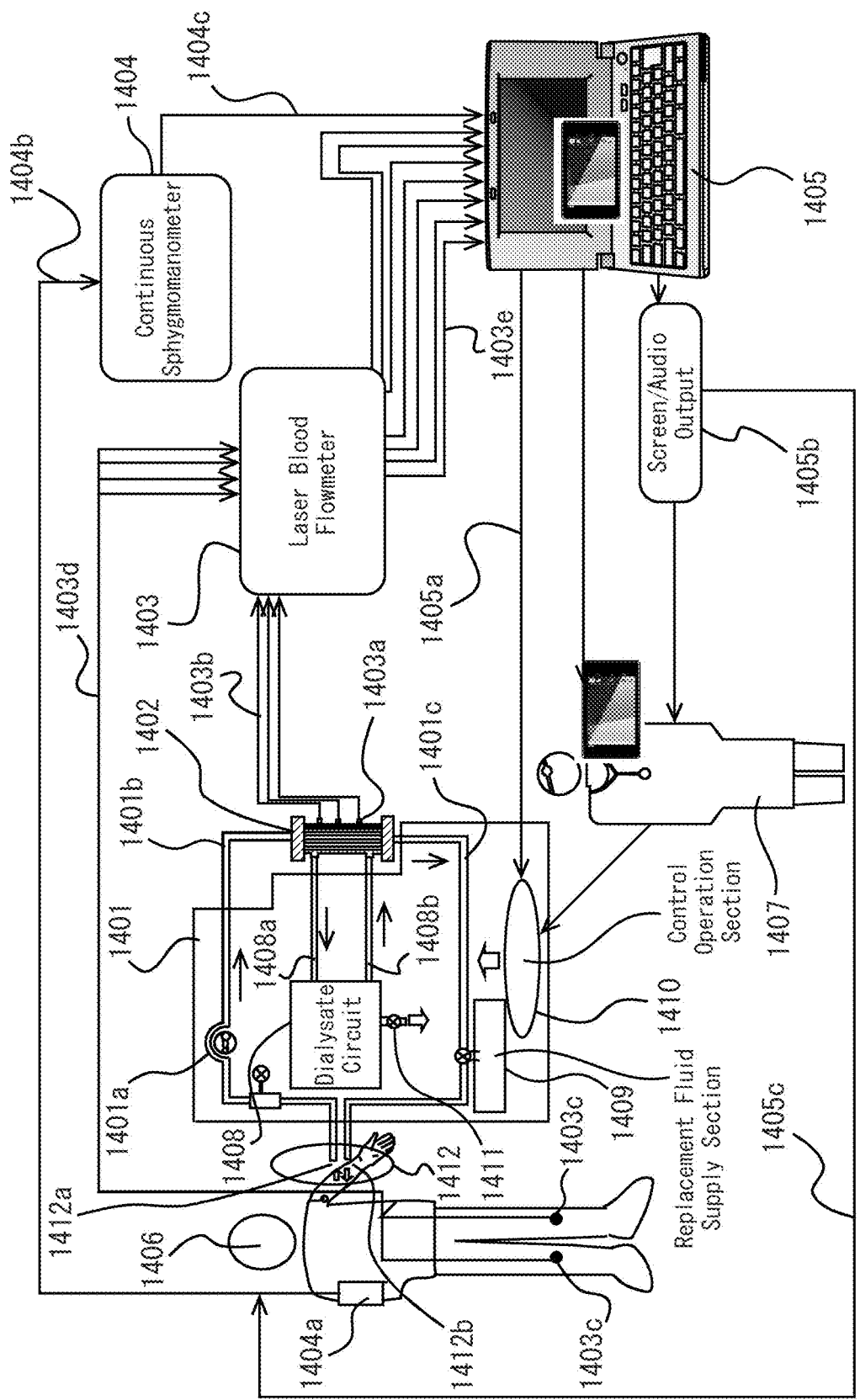
FIG. 14 is a diagram for illustrating another embodiment of the present invention.

The variation(s) in the centroid(s) is notified to the dialysis treatment personnel 1407 on the screen of computer terminal 1405 shown in FIG. 14 or by audio (screen/audio output 1405b). Alternatively, a control signal is directly output to dialysis machine 1401 (data transmission line 1405a for dialysis machine). Further, patient 1406 is also notified of the fluctuations (patient's transmission means 1405c), and asked if there is any deficiency in physical condition. By recording the response from the patient, the data can be further used as teacher data for machine learning.

Figure 18:
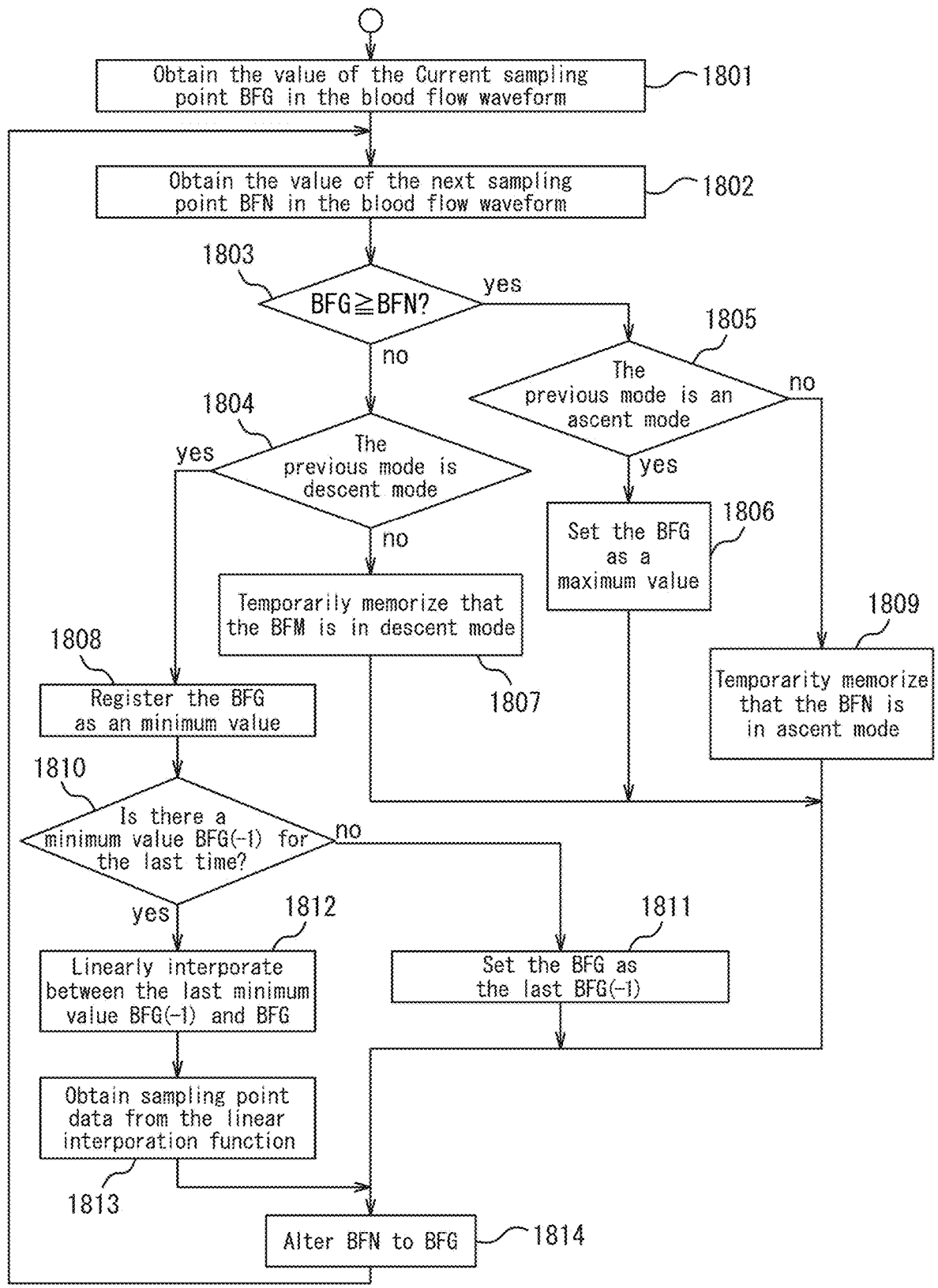
FIG. 18 is a diagram for illustrating another embodiment of the present invention.
Figure 19A:
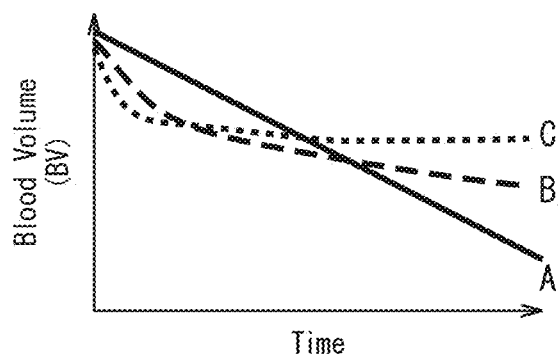
FIGS. 19A to 19E are diagrams for illustrating another embodiment of the present invention.
Figure 19B:
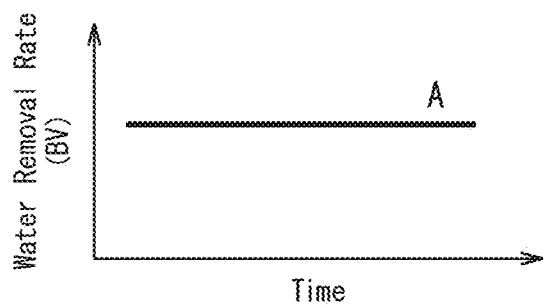
Figure 19C:
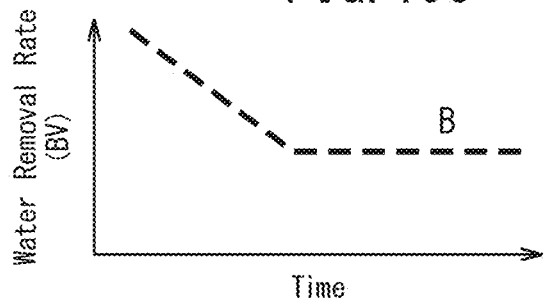
Figure 19D:
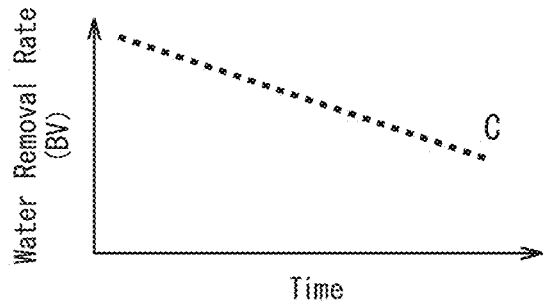
Figure 19E:
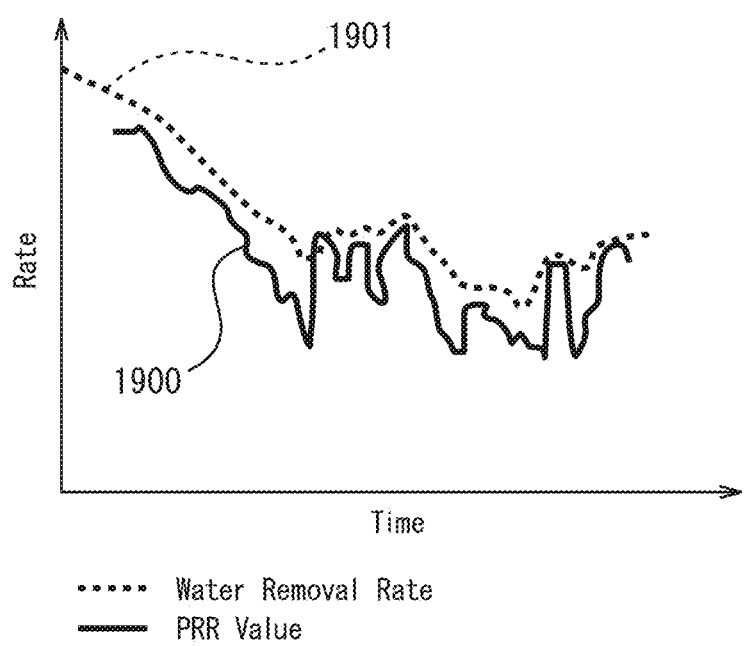

The configuration for detecting the baseline of blood flow data in the body is shown and will be explained with reference to FIG. 18. FIG. 18 shows some of the steps in detecting the baseline and converting it to data. FIG. 18 shows a flowchart for obtaining baseline data of intracorporeal blood flow data. Step 1801 is a step of obtaining blood flow values at sampling points in a blood flow waveform by sampling them at a constant time width. See FIG. 16B. A constant time interval is, for example, a time width from 100 msec to 1 minute, but other time widths may be selected. However, a longer time interval results in rougher data and less frequent detection of minimum values, whereas a shorter time range results in more segmented data and more accurate detection of minimum values, but may require more processing time. Step 1801 is a time setting for facilitating the explanation of the baseline setting operation.

Step 1802 is a step of determining the next sampling point BFN. The sampling time is the time range explained above. Step 1803 is a step of determining the size and equality between the current sampling point BFG and the next sampling point BFN. Step 1804 is a step of determining whether the previous mode is ascending or descending. The previous mode has a slope in the mode determined by the previous sampling point immediately before the current sampling point and the current sampling point.

Step 1805 is a step of determining whether the previous mode is ascending or descending. Step 1806 is a step of setting the BFG (current sampling point) as the maximum value. Step 1807 is a step of temporarily storing the fact that the next sampling point BFN is in a descent mode. Step 1808 is a step of determine that the sampling point of BFG is the minimum value. Step 1809 is a step of indicating that the BPN is in an ascent mode. Step 1810 is a step of determining whether or not there is a minimum value BFG (−1) immediately before the current sampling point. Step 1811 is a step of setting the minimum value BFG (−1) obtained for the first time after the start of measurement, if there is no minimum value by that time. Step 1812 is a step of linearly interpolating the previous minimum value BFG (−1) and the BFG. The linear interpolation means that interpolation is performed by connecting minimum values with a straight line or a curve function such as a spline curve.

Step 1813 is for obtaining data from the sampling points from the linear interpolation function, which is determined as an amplitude value with respect to time. If the time interval of the linear interpolation is long, multiple sampling points are detected between the interpolations. Step 1814 is a step of altering the sampling point BFN, which has been the next sampling point, to the current sampling point BFG in order to input the next sampling point. Note that the process for the end point of the sampling point is set after Steps 1801 and 1802, but the description is omitted to explain the interpolation operation.

Next, the operation of acquiring the baseline data of the intracorporeal blood flow data will be described according to the flowchart shown in FIG. 18. The current sampling point BFG of the intracorporeal blood flow waveform at the start of measurement is set (Step 1801). The next sampling point BFN is set (Step 1802). The slope between the current sampling point BFG and the next sampling point BFN is detected. For example, if BFG−BFN<0, the slope is upward, and if BFG−BFN>0, the slope is downward. In Step 1804, it is detected whether the slope of the sampling point immediately preceding the current sampling point BFG is upward or downward. The data of the slope of the immediately preceding sampling point uses temporarily stored data. In Step 1804, if the slope of the previous mode and the slope of the next mode are descent mode, the data is temporarily stored as descent mode (Step 1807), and when the slope is changing upward, meaning that the slope of the data has been changed by the current sampling data, the minimum BFG is registered (Step 1806).

It is detected whether or not there is a minimum value BFG (−1) before the current sample data. In the case of the first minimum value after the start of measurement, since it is the first minimum value, this minimum value BFG is set as a previous minimum value BFG (−1). If there is another previous minimum value BFG (−1), linear interpolation is performed between a linear minimum value and the next minimum value BFG (Step 1812). The linearly interpolated range is obtained by applying the predefined equation as a function of a line or curve, but since there is a time range, the data is sampled from this interval (Step 1813). The sampling at this time is exemplified by the same time interval.

If the BFG is greater than the BFN, it is in a descent mode and the previous mode is confirmed (Step 1805). If the previous mode is a descent mode, the mode is maintained as descent mode (Step 1809), and if the previous mode is in an ascent mode, the BFG indicates the maximum value (Step 1806). In this example, only minimum values are connected and sampled at a predetermined time to form a baseline from which sample points are obtained for each time, but in some cases, the middle or average value between a minimum value and a maximum values may be obtained.

By forming the baseline data from the intracorporeal blood flow waveform in this way, it is possible to smoothly perform the machine learning process with the blood pressure variation data using the pulse wave propagation velocity such as PWTT.

INDUSTRIAL APPLICABILITY

The present invention enables hemodialysis treatment at home under more comfort conditions that do not require removal and return of blood by a puncture needle, and with less burden on the patient. The present invention can also be used for early hemodialysis treatment, and enables dialysis treatment with less frequency such as once or twice a week for patients with residual renal function and a certain amount of urine. Also, for example, even a patient without residual renal function can receive hemodialysis treatment every day with less burden to the patient. Therefore, the present invention has great utility in the field of dialysis treatment.

REFERENCE SIGNS LIST

1 Percutaneous device
2 Internal shunt tubular body
3 Blood removal tubular body
4 Blood return tubular body
5 Connector
6 Blood circuit
7 Blood drive pump
8 Dialyzer
9 Lid part
10 On-off valve (opening and closing part)
11 Flow channel for blood removal
12 Flow channel for blood return
13 Blood removal side flow channel
14 Dialysate return flow channel
15 Dialysate supply flow channel
16 Blood return side flow channel.

The invention claimed is:

1. A percutaneous device comprising:
   a contact body comprising a biocompatible member which is to be contacted with a skin tissue at inside and outside a living body;
   a tubular body (2) having one end which is to be connected to an artery and an another end which is to be connected to a vein;
   a blood removal tubular body (3) for supplying blood to an external blood circuit, one end of the blood removal tubular body is to be connected to a side surface of the tubular body (2); and
   a blood return tubular body (4) having one end which is to be connected to a vein and an another end which is to be connected to a blood returning part of the blood circuit;
   wherein an another end of the blood removal tubular body (3) and said another end of the blood return tubular body (4) are arranged at the center of the contact body.

2. The percutaneous device according to claim 1, wherein the contact body is formed of hydroxyapatite or tricalcium phosphate.

3. The percutaneous device according to claim 1, wherein the tubular body (2) is formed of Gore-Tex®, expanded polytetrafluoroethylene (ePTFE), polyurethane (PU), or polyolefin-elastomer-polyester (PEP).

4. The percutaneous device according to claim 1, wherein the percutaneous device further comprises in the contact body a connector (5) comprising an upper part and a lower part that can be separated from each other.

5. The percutaneous device according to claim 4, wherein a puncture-type hollow body for blood return and a puncture-type hollow body for blood removal respectively connected to the another end of the blood return tubular body and the another end of the blood removal tubular body are arranged at the lower part of the connector.

6. The percutaneous device according to claim 4, wherein the blood return tubular body (4) and the blood removal tubular body (3) are hermetically fixed to a side surface of the connector (5).

* * * * *